(12) United States Patent
Hotchkiss et al.

(10) Patent No.: US 7,976,858 B2
(45) Date of Patent: Jul. 12, 2011

(54) DRUG DELIVERY TO A JOINT

(75) Inventors: Robert N Hotchkiss, Riverside, CT (US); John A Koski, New York, NY (US)

(73) Assignee: The Hospital for Special Surgery, New York, NY (US)

( * ) Notice: Subject to any disclaimer, the term of this patent is extended or adjusted under 35 U.S.C. 154(b) by 1732 days.

(21) Appl. No.: 11/035,375

(22) Filed: Jan. 13, 2005

(65) Prior Publication Data

US 2005/0152949 A1    Jul. 14, 2005

Related U.S. Application Data

(60) Provisional application No. 60/536,135, filed on Jan. 13, 2004, provisional application No. 60/566,737, filed on Apr. 29, 2004.

(51) Int. Cl.
*A61F 13/00* (2006.01)
*A61F 2/02* (2006.01)

(52) U.S. Cl. ................ 424/422; 623/11.11

(58) Field of Classification Search .................. None
See application file for complete search history.

(56) References Cited

U.S. PATENT DOCUMENTS

| 5,192,282 | A | 3/1993 | Draenert ................ 606/65 |
| 5,618,286 | A | 4/1997 | Brinker ................. 606/60 |
| 5,618,563 | A | 4/1997 | Berde et al. .............. 424/501 |
| 5,725,497 | A | 3/1998 | Woodruff et al. ........... 604/49 |
| 5,792,753 | A | 8/1998 | Falk et al. ............... 514/54 |
| 5,868,699 | A | 2/1999 | Woodruff et al. ........... 604/49 |
| 5,871,484 | A | 2/1999 | Spievack et al. ............ 606/60 |
| 5,902,598 | A | 5/1999 | Chen et al. ............... 424/423 |
| 5,919,196 | A | 7/1999 | Bobic et al. .............. 606/86 |
| 5,942,241 | A | 8/1999 | Chasin et al. ............. 424/426 |
| 5,960,797 | A | 10/1999 | Kramer et al. ............ 128/899 |
| 5,985,850 | A | 11/1999 | Falk et al. ............... 514/54 |
| 6,001,386 | A | 12/1999 | Ashton et al. ............. 424/423 |
| 6,051,576 | A | 4/2000 | Ashton et al. ............ 514/255.06 |
| 6,096,728 | A | 8/2000 | Collins et al. ............. 514/62 |
| 6,197,326 | B1 | 3/2001 | Suzuki et al. ............ 424/426 |
| 6,214,387 | B1 | 4/2001 | Berde et al. .............. 424/501 |

(Continued)

FOREIGN PATENT DOCUMENTS

WO    WO 00/61152    10/2000

(Continued)

OTHER PUBLICATIONS

Derendorf, H., et al., Pharmakokinetik von intraartikul/ir applizierten Glukokortikoiden, Akt. Rheumatol, 15 (1990) pp. 145-153 (English translation of abstract on first page).*

(Continued)

*Primary Examiner* — Robert A Wax
*Assistant Examiner* — Jeffrey T Palenik
(74) *Attorney, Agent, or Firm* — Wilmer Cutler Pickering Hale and Dorr LLP

(57) ABSTRACT

A method of intra-articular drug delivery may include selecting an attachment zone in a synovial joint; affixing a drug release device in the attachment zone, the drug release device comprising a base affixable in the attachment zone, a sustained-release drug carrier, and a drug, the device positioned so that the device releases the drug into the synovial fluid of the synovial joint, and so that agitation of the synovial fluid facilitates elution of the drug from the drug release device.

18 Claims, 10 Drawing Sheets

U.S. PATENT DOCUMENTS

| | | | |
|---|---|---|---|
| 6,217,911 B1 | 4/2001 | Vaugn et al. | 424/501 |
| 6,248,345 B1 | 6/2001 | Goldenheim et al. | 424/426 |
| 6,331,313 B1 | 12/2001 | Wong et al. | 424/427 |
| 6,335,035 B1 | 1/2002 | Drizen et al. | 424/488 |
| 6,346,519 B1 | 2/2002 | Petrus | 514/62 |
| 6,426,339 B1 | 7/2002 | Berde et al. | 514/180 |
| 6,428,804 B1 | 8/2002 | Suzuki et al. | 424/426 |
| 6,451,335 B1 | 9/2002 | Goldenheim et al. | 424/426 |
| 6,511,958 B1 | 1/2003 | Atkinson et al. | 514/2 |
| 6,514,415 B2 | 2/2003 | Hatch et al. | 210/695 |
| 6,514,514 B1 | 2/2003 | Atkinson et al. | |
| 6,514,516 B1 | 2/2003 | Chasin et al. | 424/426 |
| 6,521,259 B1 | 2/2003 | Chasin et al. | 424/489 |
| 6,524,606 B1 | 2/2003 | Ng et al. | 424/425 |
| 6,524,607 B1 | 2/2003 | Goldenheim et al. | 424/426 |
| 6,527,760 B1 | 3/2003 | Vad | 604/512 |
| 6,528,097 B1 | 3/2003 | Vaughn et al. | 424/501 |
| 6,528,107 B2 | 3/2003 | Chinn et al. | 427/2.24 |
| 6,534,081 B2 | 3/2003 | Goldenheim et al. | 424/426 |
| 6,544,266 B1 | 4/2003 | Roger et al. | 606/70 |
| 6,565,534 B1 | 5/2003 | Winters | 604/151 |
| 6,582,715 B1 | 6/2003 | Barry et al. | 424/422 |
| 6,590,059 B2 | 7/2003 | Ng et al. | 528/220 |
| 6,699,471 B2 | 3/2004 | Radice | 424/93.7 |
| 6,893,446 B2 * | 5/2005 | Sater et al. | 606/104 |
| 2002/0169162 A1 | 11/2002 | Smith et al. | 514/248 |
| 2003/0093157 A1 | 5/2003 | Casares et al. | 623/23.73 |
| 2003/0139811 A1 * | 7/2003 | Watson et al. | 623/11.11 |
| 2007/0053963 A1 | 3/2007 | Hotchkiss et al. | |

FOREIGN PATENT DOCUMENTS

WO    WO-2005/070333    8/2005

OTHER PUBLICATIONS

Bias, P. et al., Sustained-Release Dexamethoasone Palmitate: Pharmacokinetics and Efficacy in Patients with Activated Inflammatory Osteoarthritis of the Knee, Clin Drug Invest 2001: 21 (6); pp. 429-436.

Brown, K et al..,"A Novel Controlled-Release Intraarticular Delivery System," Arthritis and Rheumatism, Lippincott, vol. 9, Suppl., No. 36, Nov. 7, 1993, p. S267, abstract D211.

Illi, O. et al., Stimulation of Fracture Healing by Local Application of Humoral Factors Integrated in Biodegradable Implants, Eur J Pediatr Surg 8 (1998) pp. 251-255.

Christel, P., Versier, G., Landreau, Ph., and Djian, P., Osteochondral Grafting using the Mosaicplasty Technique [online], date of publication unknown [retrieved on Jan. 12, 2005]. Retrieved from the Internet: <URL: http://www.maitrise-orthop.com/corpusmaitri/orthopaedic/mo76_mosaicplasty/index.shtml>.

Non-Final Office Action mailed on Jan. 22, 2009 for U.S. Appl. No. 10/541,808, filed Jul. 8, 2005.

* cited by examiner

DRUG DELIVERY TO A JOINT

CROSS-REFERENCE TO RELATED APPLICATIONS

This application claims the benefit of U.S. Provisional Application Ser. No. 60/536,135, filed Jan. 13, 2004, and also claims the benefit of U.S. Provisional Application Ser. No. 60/566,737, filed Apr. 29, 2004. The aforementioned patent applications are hereby incorporated herein by this reference. This application is also related to U.S. application Ser. No. 10/541,808, filed Jul. 8, 2005, which claims priority to U.S. Provisional Application Ser. Nos. 60/536,135 and 60/566,737 and is a national phase application of International Application No. PCT/US2005/000999, filed Jan. 13, 2005.

INTRODUCTION

Pain and disability from arthritis, joint degeneration, and surgery have been treated by a combination of oral medications or intra-articular injections of steroid compounds designed to reduce inflammation. In addition, other devices, such as hyaluronic acid products, have been injected to provide visco-supplementation. Unfortunately, these approaches have significant systemic side effects or are not effective for extended periods of time.

In order to provide local or regional blockade for extended periods, clinicians currently use local anesthetics administered through a catheter or syringe to a site where the pain is to be blocked. This requires repeated administration where the pain is to be blocked over a period of greater than one day, either as a bolus or through an indwelling catheter connected to an infusion pump. These methods have the disadvantage of potentially causing irreversible damage to nerves or surrounding tissues due to fluctuations in concentration and high levels of anesthetic. In addition, anesthetic administered by these methods are generally neither confined to the target area, nor delivered in a linear, continuous manner. In all cases, analgesia rarely lasts for longer than six to twelve hours, more typically four to six hours. In the case of a pump, the infusion lines are difficult to position and secure, the patient has limited, encumbered mobility and, when the patient is a small child or mentally impaired, they may accidentally disengage the pump.

In part, this disclosure describes implantable devices that may be used to deliver drugs to a joint.

SUMMARY

In one aspect, this disclosure describes devices and methods for delivering drugs to the synovial fluid of a joint by locally implanting a drug delivery device. In certain embodiments, the device is positioned in such a way that agitation of synovial fluid facilitates elution of the drug from the device.

In one aspect, a method of intra-articular drug delivery includes selecting an attachment zone in a synovial joint and affixing a drug release device in the attachment zone. Exemplary suitable attachment zones include intra-articular regions of the synovial joint where there is no interfacing articular cartilage. In certain instances, an attachment zone may include intra-articular regions of bone that are non-load-bearing and optionally removed from the articulation surface. In certain embodiments, the drug release device includes a base affixable in the attachment zone, a sustained-release drug carrier, and a drug. The device may be positioned, in certain applications, so that the device releases the drug into the synovial fluid of the synovial joint, and further, so that agitation of the synovial fluid may facilitate elution of the drug from the drug release device.

In a further aspect, a method of providing a therapeutic to a skeletal articulation includes identifying a safe zone of the articulation and coupling a therapeutic elution apparatus in the safe zone. Exemplary safe zones include non-load-bearing regions in or around the articulation. In certain embodiments, the therapeutic elution apparatus includes a body couplable in the safe zone, and a therapeutic dispersed in a controlled-release binder. The apparatus may be positioned, in certain applications, so that it releases the therapeutic into the articulation environment.

In another aspect, a drug delivery device includes a base and a sustained-release drug carrier coupled to the base. In certain embodiments, the base may be so sized and shaped as to be capable of affixation in an attachment zone of a synovial joint. Typically, the carrier includes a drug to be eluted in vivo, often into the synovial fluid upon implantation of the device in a joint. In certain applications, the carrier may be so formed as to elute the drug into synovial fluid sufficient to sustain a therapeutically effective concentration of the drug in the synovial fluid for at least 8 hours.

In yet another aspect, a wide range of therapeutic drugs are contemplated, including but not limited to antiinflammatories, antiinfectives, analgesics, and anesthetics. A wide range of drug carrier materials are contemplated, including but not limited to polymers, such as polytetrafluoroethylene, polyfluorinated ethylenepropylene, polylactic acid, polyglycolic acid, silicone, and mixtures thereof.

In still another aspect, a drug delivery device may be delivered by a wide variety of methods, such as by placement into a drill site, or forceful injection by gun. In an embodiment, a method of intra-articular drug delivery may include selecting an attachment zone in a synovial joint, and affixing a drug release device in the attachment zone, the drug release device comprising a base affixable in the attachment zone, a sustained-release drug carrier, and a drug, the device positioned so that the device releases the drug into the synovial fluid of the synovial joint, and so that agitation of the synovial fluid facilitates elution of the drug from the drug release device.

In any preceding embodiment, the attachment zone may include a non-articulating portion of bone and/or cartilage within the synovial joint.

Any preceding embodiment may further include removing the bone and/or cartilage in the attachment zone to create a void, and so inserting the drug release device into the void that at least one surface of the drug release device is in communication with the synovial fluid.

In any preceding embodiment, the drug release device may be so inserted that its surface in communication with the synovial fluid is about flush with surrounding bone and/or cartilage.

In any preceding embodiment, the attachment zone may include a band of bone and/or cartilage adjacent to an articulating surface within the synovial joint.

In any preceding embodiment, the band may extend from about 0.5 millimeters to about 1 centimeter away from the articulating surface.

In any preceding embodiment, the synovial joint may be a hip joint, and the attachment zone may include a non-articulating portion of bone and/or cartilage within the hip.

In any preceding embodiment, the attachment zone may include a band of bone and/or cartilage adjacent to at least one of a femoral head, and an acetabulum.

In any preceding embodiment, the synovial joint may be a knee joint, and the attachment zone may include a non-articulating portion of bone and/or cartilage within the knee.

In any preceding embodiment, the attachment zone may include a band of bone and/or cartilage adjacent to at least one of a tibial plateau, a femoral condyle, a patellofemoral area, the medial rim of a femoral trochlea, the lateral rim of a femoral trochlea, and the periphery of an intercondylar notch.

In any preceding embodiment, the synovial joint may be a shoulder joint, and the attachment zone comprises a non-articulating portion of bone and/or cartilage within the shoulder.

In any preceding embodiment, the attachment zone may include a band of bone and/or cartilage adjacent to at least one of the anatomical neck of a humerus, a glenoid cavitym and a glenoid neck.

In any preceding embodiment, the synovial joint may be an arthroplastic joint comprising at least one prosthesis, and the attachment zone comprises a non-articulating portion of bone and/or cartilage within the joint.

In any preceding embodiment, wherein the attachment zone may include a band of bone and/or cartilage adjacent to the at least one prosthesis.

In any preceding embodiment, the drug release device may be forcefully injected by gun.

In any preceding embodiment, the drug release device may include threads on its outer surface, and the drug release device may be affixed by drilling a hole in the attachment zone and screwing the drug release device into the hole.

In any preceding embodiment, the drug release device may include a base, so sized and shaped as to be affixable in an attachment zone of a synovial joint, and a sustained-release drug carrier coupled to the base, the carrier including a drug, the carrier so formed as to elute the drug into synovial fluid, upon implantation of the device in a joint, sufficient to sustain a therapeutically effective concentration of the drug in the synovial fluid for at least 8 hours.

DETAILED DESCRIPTION

1. Overview

Figure 1:
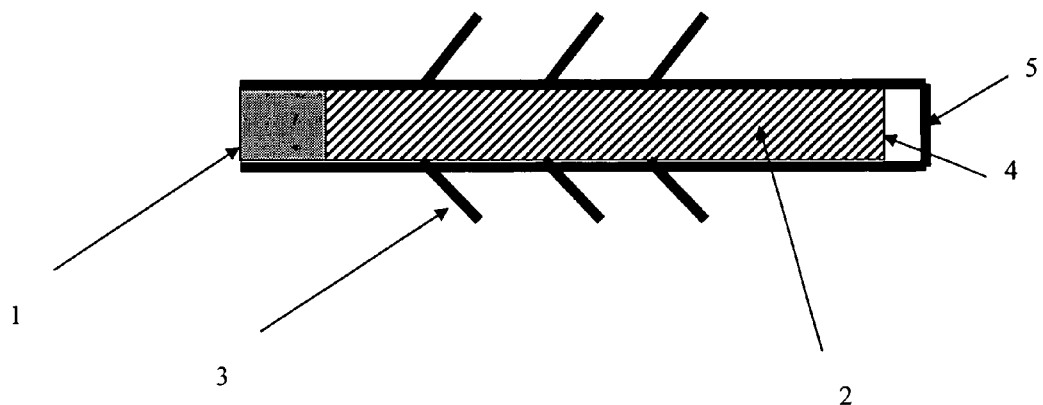
FIG. 1 depicts a cross section of an exemplary intra-articular drug delivery device.

The present disclosure provides devices and methods for delivering drugs to joints, particularly synovial joints. In part, this disclosure provides controlled-release devices that are capable of being implanted in the joint to deliver therapeutic agents, often to the synovial fluid. In certain examples, the devices, when implanted, are capable of providing sustained drug release of therapeutic agents into the synovial fluid of the affected joint for the relief of pain, reduction of inflammation, the enhancement of joint lubrication, the treatment of infection, and/or the treatment or prevention of other diseases or conditions.

In a preferred embodiment, a device is implanted within a joint into bone in an area that is substantially exposed to synovial fluid flow, preferably allowing sustained elution of the therapeutic compound into the synovial fluid and a substantially even distribution of the desired therapeutic within the joint. In certain instances, the implantation site is constantly exposed to synovial fluid flow.

Each joint contains specified areas defined hereafter as "attachment zones" that permit drilling, anchoring, or other types of affixing of a device. Certain attachment zones will not cause substantial damage to the load-bearing or articulating cartilage or other surfaces of the specified joint. In certain embodiments, the placement and location of the device does not cause material damage to the cartilage surface, as it may placed and secured using an anchoring device that fixes the device to bone, in the joint cavity, but not into or on the articulating surface of the joint in a manner that could cause such damage while the device is in place.

The controlled release devices may be biocompatible and may be capable of being implanted or otherwise placed into a joint. In an exemplary embodiment, a device may have a core including a drug/polymer composition and an outer layer along the long axis of the device that is substantially impermeable to the entrance of an environmental fluid and substantially impermeable to the release of the drug during a delivery period, with drug release possible across a short axis plane of the device, which axis or end of the device may be exposed to synovial fluid upon placement. In certain instances, the end of the device may have a semipermeable membrane or alternatively it may expose the core directly. In certain instances, the short axis plane of a device may account for a minority, such as no more than about 10%, no more than about 20%, no more than about 30%, no more than about 40%, or less than 50%, of the total surface area of the device. The device can be so sized and shaped, and formed of such materials, as to facilitate delivering a variety of drugs with varying degrees of solubility and molecular weight. Methods are also provided for using these drug delivery devices.

In certain aspects, the devices may be implanted in regions of a joint that are non-load-bearing and/or that do not form part of the cartilaginous articulation surfaces of bones. In further examples, the devices may be anchored to and recessed within bone either fully or in part. In certain instances, usually when recessed fully, the portion of the device's surface exposed to the synovial fluid is substantially flush with the bone surface. In still further embodiments, the devices may be positioned in a joint so that agitation of synovial fluid past or through the exposed surface facilitates elution of a therapeutic incorporated in the device. In other examples, the one or more therapeutics may be formulated for sustained release, such as by impregnating them in a matrix, or mixing them with a suitable composition, such as a polymer.

2. Definitions

For convenience, before further description of exemplary embodiments, certain terms employed in the specification, examples, and appended claims are collected here. These definitions should be read in light of the remainder of the disclosure and understood as by a person of skill in the art.

The articles "a" and "an" are used herein to refer to one or to more than one (i.e., to at least one) of the grammatical object of the article. By way of example, "an element" means one element or more than one element.

The term "access device" is an art-recognized term and includes any medical device adapted for gaining or maintaining access to an anatomic area. Such devices are familiar to artisans in the medical and surgical fields. An access device may be a needle, a catheter, a cannula, a trocar, a tubing, a shunt, a drain, or an endoscope such as an otoscope, nasopharyngoscope, bronchoscope, or any other endoscope adapted for use in the joint area, or any other medical device suitable for entering or remaining positioned within the preselected anatomic area.

The terms "biocompatible polymer" and "biocompatibility" when used in relation to polymers are art-recognized. For example, biocompatible polymers include polymers that are generally neither themselves toxic to the host, nor degrade (if the polymer degrades) at a rate that produces monomeric or oligomeric subunits or other byproducts at toxic concentrations in the host. In certain embodiments, biodegradation generally involves degradation of the polymer in a host, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1M NaOH at 37° C. until complete degradation is observed. The solution is then neutralized with 1M HCl. About 200 µL of various concentrations of the degraded sample products are placed in 96-well tissue culture plates and seeded with human gastric carcinoma cells (GT3TKB) at $10^4$/well density. The degraded sample products are incubated with the GT3TKB cells for 48 hours. The results of the assay may be plotted as % relative growth vs. concentration of degraded sample in the tissue-culture well. In addition, polymers and formulations may also be evaluated by well-known in vivo tests, such as subcutaneous implantations in rats to confirm that they do not cause significant levels of irritation or inflammation at the subcutaneous implantation sites.

The term "biodegradable" is art-recognized, and includes polymers, compositions and formulations, such as those described herein, that are intended to degrade during use. Biodegradable polymers typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to side chain or that connects a side chain to the polymer backbone. For example, a therapeutic agent or other chemical moiety attached as a side chain to the polymer backbone may be released by biodegradation. In certain embodiments, one or the other or both generally types of biodegradation may occur during use of a polymer. As used herein, the term "biodegradation" encompasses both general types of biodegradation.

The degradation rate of a biodegradable polymer often depends in part on a variety of factors, including the chemical identity of the linkage responsible for any degradation, the molecular weight, crystallinity, biostability, and degree of cross-linking of such polymer, the physical characteristics of the implant, shape and size, and the mode and location of administration. For example, the greater the molecular weight, the higher the degree of crystallinity, and/or the greater the biostability, the biodegradation of any biodegradable polymer is usually slower. The term "biodegradable" is intended to cover materials and processes also termed "bioerodible".

In certain embodiments, if the biodegradable polymer also has a therapeutic agent or other material associated with it, the biodegradation rate of such polymer may be characterized by a release rate of such materials. In such circumstances, the biodegradation rate may depend on not only the chemical identity and physical characteristics of the polymer, but also on the identity of any such material incorporated therein.

In certain embodiments, polymeric formulations biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between 25 and 37° C. In other embodiments, the polymer degrades in a period of between about one hour and several weeks, depending on the desired application.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "drug delivery device" is an art-recognized term and refers to any medical device suitable for the application of a drug to a targeted organ or anatomic region. The term includes those devices that transport or accomplish the instillation of the compositions towards the targeted organ or anatomic area, even if the device itself is not formulated to include the composition. As an example, a needle or a catheter through which the composition is inserted into an anatomic area or into a blood vessel or other structure related to the anatomic area is understood to be a drug delivery device. As a further example, a stent or a shunt or a catheter that has the composition included in its substance or coated on its surface is understood to be a drug delivery device. A drug delivery device can include a rigid or flexible container. It may include a semi-solid composition that release drug by dissolution of the device or by leaching of drug from the device. We should also be clear that "implant" covers attaching to the joint in any way, e.g., by implanting into a cavity in bone or cartilage or by suturing or otherwise adhering the device to the surface of bone, tendon, or cartilage.

When used with respect to a therapeutic agent or other material, the term "sustained release" is art-recognized. For example, a subject composition that releases a substance over time may exhibit sustained release characteristics, in contrast to a bolus type administration in which the entire amount of the substance is made biologically available at one time. For example, in particular embodiments, upon contact with body fluids including blood, tissue fluid, lymph or the like, the polymer matrices (formulated as provided herein and otherwise as known to one of skill in the art) may undergo gradual degradation (e.g., through hydrolysis) with concomitant release of any material incorporated therein, for a sustained or extended period (as compared to the release from a bolus). This release may result in prolonged delivery of therapeutically effective amounts of any incorporated a therapeutic agent. Sustained release will vary in certain embodiments as described in greater detail below.

The term "delivery agent" is an art-recognized term, and includes molecules that facilitate the intracellular delivery of a therapeutic agent or other material. Examples of delivery agents include: sterols (e.g., cholesterol) and lipids (e.g., a cationic lipid, virosome or liposome).

The term "or" as used herein should be understood to mean "and/or", unless the context clearly indicates otherwise.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "fluid" is art-recognized to refer to a non-solid state of matter in which the atoms or molecules are free to move in relation to each other, as in a gas or liquid. If unconstrained upon application, a fluid material may flow to assume the shape of the space available to it, covering for example, the surfaces of an excisional site or the dead space left under a flap. A fluid material may be inserted or injected into a limited portion of a space and then may flow to enter a larger portion of the space or its entirety. Such a material may be termed "flowable." This term is art-recognized and includes, for example, liquid compositions that are capable of being sprayed into a site; injected with a manually operated syringe fitted with, for example, a 23-gauge needle; or delivered through a catheter. Also included in the term "flowable" are those highly viscous, "gel-like" materials at room temperature that may be delivered to the desired site by pouring, squeezing from a tube, or being injected with any one of the commercially available injection devices that provide injection pressures sufficient to propel highly viscous materials through a delivery system such as a needle or a catheter. When the polymer used is itself flowable, a composition comprising it need not include a biocompatible solvent to allow its dispersion within a body cavity. Rather, the flowable polymer may be delivered into the body cavity using a delivery system that relies upon the native flowability of the material for its application to the desired tissue surfaces. For example, if flowable, a composition comprising polymers can be injected to form, after injection, a temporary biomechanical barrier to coat or encapsulate internal organs or tissues, or it can be used to produce coatings for solid implantable devices. In certain instances, flowable subject compositions have the ability to assume, over time, the shape of the space containing it at body temperature.

Viscosity is understood herein as it is recognized in the art to be the internal friction of a fluid or the resistance to flow exhibited by a fluid material when subjected to deformation. The degree of viscosity of the polymer may be adjusted by the molecular weight of the polymer and other methods for altering the physical characteristics of a specific polymer will be evident to practitioners of ordinary skill with no more than routine experimentation. The molecular weight of the polymer used may vary widely, depending on whether a rigid solid state (higher molecular weights) desirable, or whether a fluid state (lower molecular weights) is desired.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.,* 66:1-19 (1977).

A "patient," "subject," or "host" to be treated by the subject method may mean either a human or non-human animal, such as primates, mammals, and vertebrates.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The term "synovial joint" refers to a moveable articulation of two or more bones. The articulation is defined by a synovial cavity, which contains a volume of synovial fluid, is lined with a synovial membrane, and is surrounded by a fibrous capsule. The opposing bone surfaces are each covered with a layer of cartilage. The cartilage and synovial fluid reduce friction between the articulating bone surfaces and enable smooth movements. Synovial joints can be further distinguished by their shape, which controls the movements they allow. For example, hinge joints act like the hinge on a door, allowing flexion and extension in just one plane. An example is the elbow between the humerus and the ulna. Ball and socket joints, such as the hip, allow movement in several planes simultaneously. Condyloid (or ellipsoid) joints, such as the knee, permit motion in more than one plane in some positions but not others. For example, no rotation is possible in the extended knee, but some rotation is possible when the knee is flexed. Pivot joints, such as the elbow (between the radius and the ulna), allow one bone to rotate around another. Saddle joints, such as at the thumb (between the metacarpal and carpal) are so named because of their saddle shape, and allow movement in a variety of directions. Finally, gliding joints, such as in the carpals of the wrist, allow a wide variety of movement, but not much distance.

Synovial joints include but are not limited to shoulder (glenohumeral and acromioclavicular), elbow (ulno-humeral, radio-capitellar and proximal radioulnar), forearm (radioulnar, radiocarpal, ulnocarpal), wrist (distal radioulnar, radio-carpal, ulno-carpal, mid carpal), hand (carpo-metacarpal, metocarpophalangeal, interphalangeal), spine (intervertebral), hip, knee, ankle (tibiotalar, tibiofibular), and foot (talocalcaneal, talonavicular, intertarsal, tarso-metatarsal, metatarsal-phalangeal, interphalangeal).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition, such as joint pain, degeneration, inflammation, or infection. The terms include without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" is an art-recognized term. In certain embodiments, the term refers to an amount of a therapeutic agent that, when incorporated into a polymer, produces some desired effect at a reasonable benefit/risk ratio applicable to any medical treatment. In certain embodiments, the term refers to that amount necessary or sufficient to eliminate, reduce or maintain (e.g., prevent the spread of) a tumor or other target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation.

The term "preventing", when used in relation to a condition, such as a local recurrence, a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population.

"Radiosensitizer" is defined as a therapeutic agent that, upon administration in a therapeutically effective amount, promotes the treatment of one or more diseases or conditions that are treatable with electromagnetic radiation. In general, radiosensitizers are intended to be used in conjunction with electromagnetic radiation as part of a prophylactic or therapeutic treatment. Appropriate radiosensitizers to use in conjunction with treatment with the subject compositions will be known to those of skill in the art.

"Electromagnetic radiation" as used in this specification includes, but is not limited to, radiation having the wavelength of $10^{-20}$ to 10 meters. Particular embodiments of electromagnetic radiation employ the electromagnetic radiation of: gamma-radiation ($10^{-20}$ to $10^{-13}$ m), x-ray radiation ($10^{-11}$ to $10^{-9}$ m), ultraviolet light (10 m to 400 nm), visible light (400 nm to 700 nm), infrared radiation (700 nm to 1.0 mm), and microwave radiation (1 mm to 30 cm).

The phrases "systemic administration," "administered systemically," "peripheral administration" and "administered peripherally" are art-recognized, and include the administration of a subject composition or other material at a site remote from the disease being treated. Administration of an agent directly into, onto or in the vicinity of a lesion of the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

In certain embodiments, a therapeutically effective amount of a therapeutic agent for in vivo use will likely depend on a number of factors, including: the rate of release of the agent from the polymer matrix, which will depend in part on the chemical and physical characteristics of the polymer; the identity of the agent; the mode and method of administration; and any other materials incorporated in the polymer matrix in addition to the agent.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The terms "incorporated" and "encapsulated" are art-recognized when used in reference to a therapeutic agent and a polymeric composition, such as a composition disclosed herein. In certain embodiments, these terms include incorporating, formulating or otherwise including such agent into a composition which allows for sustained release of such agent in the desired application. The terms may contemplate any manner by which a therapeutic agent or other material is incorporated into a polymer matrix, including for example: attached to a monomer of such polymer (by covalent or other binding interaction) and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of a therapeutic agent or other material and at least one other a therapeutic agent or other material in a subject composition.

More specifically, the physical form in which a therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in a controlled-release polymer that it is dispersed as small droplets, rather than being dissolved, in the polymer. Any form of encapsulation or incorporation is contemplated by the present disclosure, in so much as the sustained release of any encapsulated therapeutic agent or other material determines whether the form of encapsulation is sufficiently acceptable for any particular use.

The term "biocompatible plasticizer" is art-recognized, and includes materials which are soluble or dispersible in the controlled-release compositions described herein, which increase the flexibility of the polymer matrix, and which, in the amounts employed, are biocompatible. Suitable plasticizers are well known in the art and include those disclosed in U.S. Pat. Nos. 2,784,127 and 4,444,933. Specific plasticizers include, by way of example, acetyl tri-n-butyl citrate (c. 20 weight percent or less), acetyl trihexyl citrate (c. 20 weight percent or less), butyl benzyl phthalate, dibutyl phthalate, dioctylphthalate, n-butyryl tri-n-hexyl citrate, diethylene glycol dibenzoate (c. 20 weight percent or less) and the like.

"Small molecule" is an art-recognized term and refers to a molecule which has a molecular weight of less than about 2000 amu, or less than about 1000 amu, and even less than about 500 amu.

3. Implant Structure

A wide variety of structures may be employed for providing drug delivery to synovial joints. Typically, a drug delivery device may include a base that is so sized and shaped as to be affixable in the synovial joint, and a drug carrier coupled to the base that includes a therapeutic drug.

An exemplary implantable intra-articular drug delivery device is depicted in FIG. 1. As shown in this exemplary embodiment, the base of the device may include a housing (5), and the drug carrier may include a mass (4). The mass (4) may be disposed inside the housing. In some instances, the mass (4) may be a cartridge. For example, the cartridge may be manufactured separately from the housing and later inserted into the housing. The cartridge or mass (4) may be replaceable, so that the drug carrier may be removed from the device without disturbing the housing's affixation in a joint.

The outer layer of the mass (4) may be formed at least in part by a material substantially impermeable to the drug and/or environmental fluids (such as synovial fluid in a joint). The material may include a polymer. Examples of polymers include polytetrafluoroethylene, polyfluorinated ethylenepropylene, polylactic acid, polyglycolic acid, silicone, and mixtures thereof.

The mass (4) may have a surface (1) exposed to the environment, such as synovial fluid. The surface (1) may be covered at least in part by a membrane, such as a semi-permeable membrane. The membrane may be formed to prevent particulate materials, such as biodegradable polymer, from passing out of the drug carrier and into the synovial fluid, while permitting the drug released from the carrier (2) to pass out of the cartridge and in to the joint. This filter may take consist of a semi-permeable, osmotic membrane or a porous cellulose filter such as a Millipore filter.

In certain embodiments, the housing (5) may be made at least in part of a biocompatible material. Furthermore, in some embodiments, the housing (5) may be made of an implantable material, such as a material suitable for implantation in bone, implantation in cartilage, and/or implantation in other biomaterials in a joint. In certain embodiments, the housing is formed at least in part of a material of sufficient strength to be implanted into bone without damage. In particular, the housing may be formed at least in part of a material that can maintain the housing's integrity during implantation. This may help prevent leakage of a drug in the carrier through a crack or fissure in the housing. In some embodiments, the reservoir housing may be constructed from a metal, such as titanium, nickel titanium, stainless steel, anodized aluminum, or tantalum, or a plastic, such as polyethylene, nylon, or polyurethane. Alternatively a composite or ceramic may be used. The housing may also include a material or modified material to allow for osseous integration of the implant—i.e., bone ingrowth. Other suitable materials will be apparent to one of ordinary skill in the art. Moreover, combinations of materials may be used.

In certain embodiments, the device may be affixable in an attachment zone of a joint. As depicted in FIG. 1, the housing (5) may include one or more barbs (3). The barb or barbs (3) may lodge in and/or against, for example, a bony surface, and thereby minimize the device's motion relative to the bone. In some embodiments, barbs (3) may be axially aligned. They may be circumferentially spaced in relation to each other about the base.

In some embodiments, the barb or barbs may be able to adopt different states; in some states, the barbs may be retracted or otherwise disposed to facilitate mobility and positioning of the device; in other states, the barbs may be expanded or otherwise disposed to facilitate lodgment and immobility of the device. The barb or barbs may be transitionable between one or more such states. For example, a barb may have a first, or "retracted" state, in which the barb's span lies close enough to the device as not to impede positioning the device. The barb may have a second, or "expanded" state, in which the barb's free end so protrudes from the device as to impinge surrounding anatomy, thereby promoting affixation of the device.

In some embodiments, the barb may me deformable among various states. For example, a barb may be biased toward a particular state. A barb may be constrained to an unbiased state and allowed to assume a biased state when the constraint is removed. In some embodiments, a constraint may be mechanical, such as a sleeve or an adhesive. In some embodiments, a constraint may be chemical, so that the barb changes configuration in response to a chemical reaction. In some embodiments, the barb may have a shape memory. A shape memory may be dependent, for example, on temperature. In one embodiment, a barb may assume a "retracted" state below attachment zone temperature and an "expanded" state at attachment zone temperature, so that disposition of a device in an attachment zone causes the barb to transition from the retracted state to the expanded state. A barb may be elastically or plastically deformable; a barb may be reversibly or irreversible deformable.

In the embodiment depicted in FIG. 1, the barbs extend rearwardly and radially outwardly from the body. In some embodiments, the barb end(s) may extend to positions outside a longitudinal projection of the largest geometric cross-section of the body transverse to its longitudinal axis.

Barbs (3) may be formed at least in part by a wide variety of materials. Examples include materials disclosed in U.S. Pat. No. 4,665,906 entitled "Medical Devices Incorporating SIM Alloy Elements", issued May 19, 1987 to Jervis. Other exemplary materials are nickel-titanium alloys, such as nitinol. The combination of the material and orientation of the barbs on the reservoir housing can help the barbs to "spring back" toward their normal, unstressed condition after the insertion process of the device into bone, for example, is complete.

The device may include other features to make it affixable in an attachment zone of a joint. For example, the base may have a variable diameter. The device may adopt a first diameter to facilitate insertion, and a second diameter to facilitate affixation. The device may be provided with an adhesive, such as bone cement, that promotes adhesion of the device to the material of the attachment zone. The device may be provided with cells, growth factors, cytokines, or other biomaterials to promote infiltration and anchoring of the device by host tissue.

Figure 2:
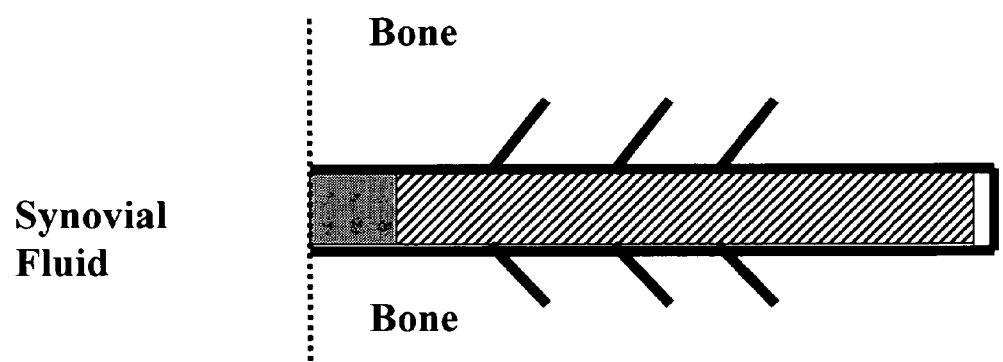
FIG. 2 depicts an exemplary positioning of an intra-articular drug delivery device.

The device of this exemplary embodiment may be embedded in a bone such that the device's surface is flush with the surrounding bone, and so that the semipermeable membrane faces the synovial cavity. A schematic depiction of this orientation is shown in FIG. 2. The device may be thus positioned so as not to present an obstruction for potential interference with joint motion. Furthermore, when so positioned, the device may be exposed to synovial fluid through the semipermeable membrane. Thus, as synovial fluid flows over the membrane, diffusion of therapeutic agent may occur. In addition, synovial fluid can infiltrate the device through the membrane and thus provide fluid communication for the agent to reach the synovial fluid.

In preferred embodiments, a sustained drug delivery device for intraarticular use may have a cross-sectional diameter in the range of about 0.5 mm to about 5 mm. It may have a length in the range of about 3 mm to about 20 mm.

Other structures are contemplated. In one exemplary embodiment, the device includes a base coated with the drug carrier. In another exemplary embodiment, the device may be so sized and shaped to be a prosthetic replacement for all or a portion of a bone. For example, the device base may be a portion of a femur used in a total knee replacement. Many other examples of bone prosthetics will be readily apparent to one of ordinary skill in the art. The drug carrier is coupled to the base as described above. Alternatively, the prosthetic base can define a recess into which a drug carrier, such as a modular cartridge, may be placed.

Figure 9:
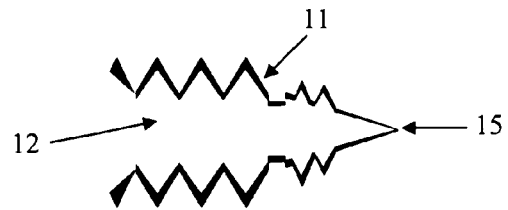
FIGS. 9-11A depict exemplary drug delivery devices and components.
Figure 10:
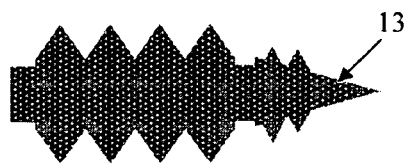
Figure 11:
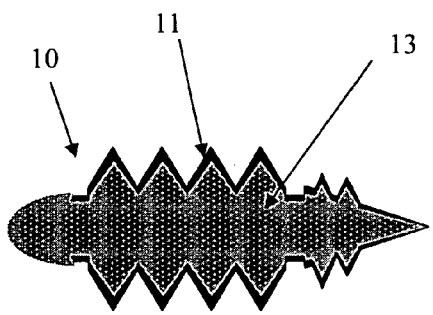

FIGS. 9-11 depict other embodiments of drug delivery devices. In one embodiment, the device 10 may include a stage/housing 11. The stage 11 may be externally threaded. The external threads can help keep the stage in position. For example, the threaded stage could be screwed into a pre-drilled hole in an attachment zone. Alternatively, the device could be inserted in a self boring/self tapping manner, in the recipient attachment zone. The stage may include a tip, such as a sharpened tip 15, suitable for this purpose.

Figure 11A:
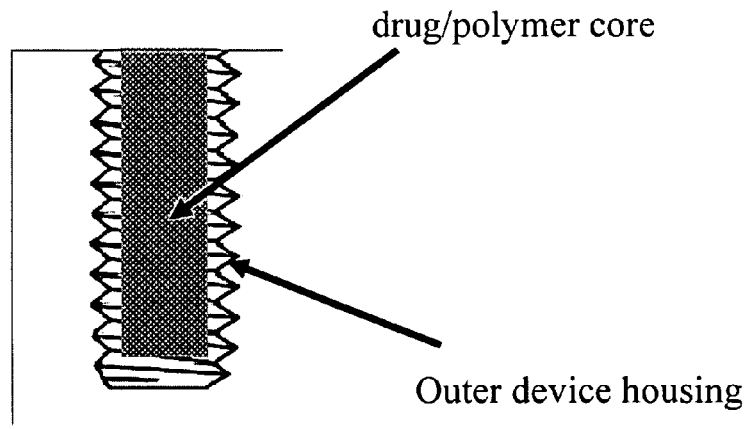

FIG. 11a shows another embodiment of a drug delivery device. The housing may include an outer threaded surface and inner threaded or smooth surface. The housing may define an inner cavity. A plug of drug/polymer mixture may be placed the cavity. The inner threads on the housing facilitate anchoring the plug and may also facilitate removal and exchange of a cartridge with the drug polymer mixture.

Figure 4:
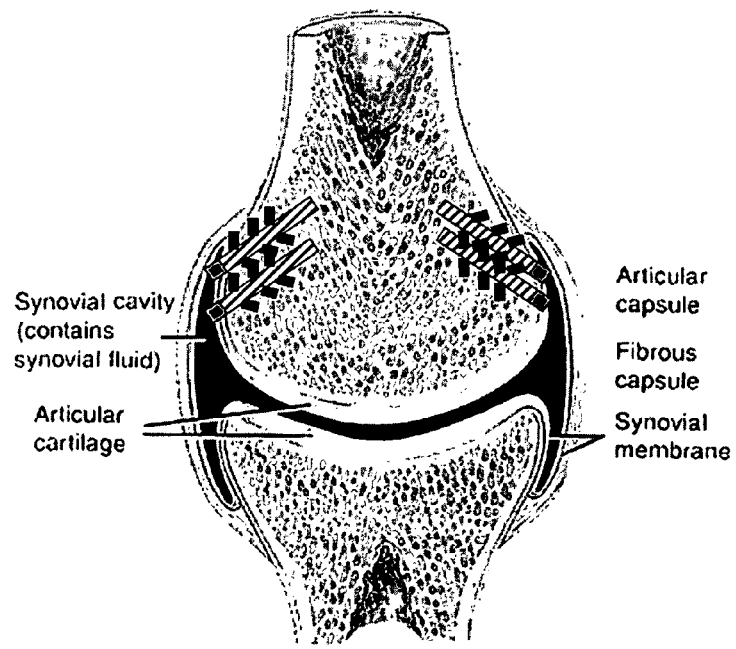
FIG. 4 depicts a cross section of a knee joint showing exemplary placements of an intra-articular drug delivery device.
Figure 12:
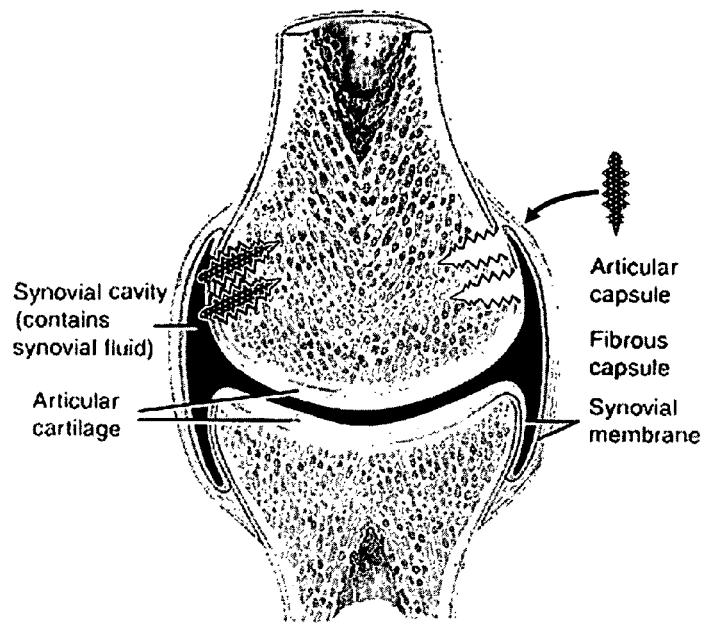
FIGS. 12-13 depict exemplary placements of drug delivery devices.

FIG. 12 shows some exemplary placements of threaded devices, similar to those shown in FIG. 4.

The stage 11 may also include a central socket 12. The central socket may be threaded. A drug implant 13 may be disposed in the central socket 12. The implant 13 may have the same or similar shape as the socket 12 to help it remain in position. For example, the implant can be molded with threads on its body to match the recipient threads of the socket of the stage. The threads may be machined to have a thread interval or "pitch" of about 0.25 mm to 1.5 mm and can vary to about 0.1 mm to 0.25 mm at the lower end of the implant. The threads may have flat top lands with a nominal width of about 0.10 mm to 0.15 mm.

The implant 13 can be removed and/or replaced when it has degraded, when the drug is degraded, exhausted, or being delivered in subtherapeutic concentration, or when the need or desirability has passed for the particular drug being eluted. The insert may be held in the stage by the aforementioned threading. In one embodiment, a differential thread pitch can be provided to "lock" the insert in place, to preclude loosening and escape into the joint space.

In certain embodiments, the device can have an outer diameter in the range of about 1 mm to about 10 mm. In certain embodiments, the device can have a length of about 3 mm to about 2 cm.

Figure 13:
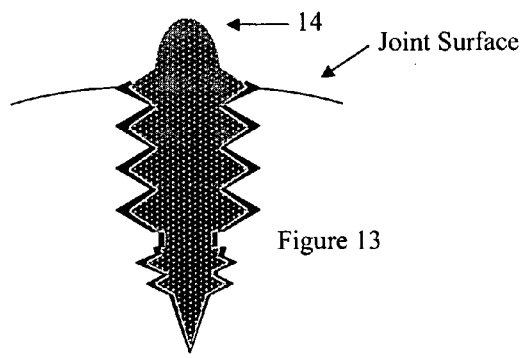

As shown in FIG. 13, The cap of the drug/polymer insert may include a rounded surface 14. This surface can reduce physical interaction with surrounding soft tissue. This surface can also expose an adequate surface for drug elution and desired pharmacokinetic release.

4. Attachment Zones

As discussed above, each joint contains specified areas defined hereafter as "attachment zones" that permit drilling, anchoring, or other types of affixing of a device. Certain attachment zones will not cause substantial damage to the load-bearing or articulating cartilage or other surfaces of the specified joint. In certain embodiments, the placement and location of the device does not cause material damage to the cartilage surface, as it may be placed and secured using an anchoring device that fixes the device to bone, in the joint cavity, but not into or on the articulating surface of the joint in a manner that could cause such damage while the device is in place.

In some embodiments, an attachment zone may be an intra-articular region of a synovial joint where there is no interfacing articular cartilage. It may be located, for example, in a bone portion that is non-load-bearing and removed from the articulation surface of the synovial joint. The device may be attached at an attachment zone within the synovial joint, allowing for continuous exposure to synovial fluid flow and resulting release of therapeutic, without damaging the articular surface that is in apposition during range of motion of the given joint.

Figure 3:
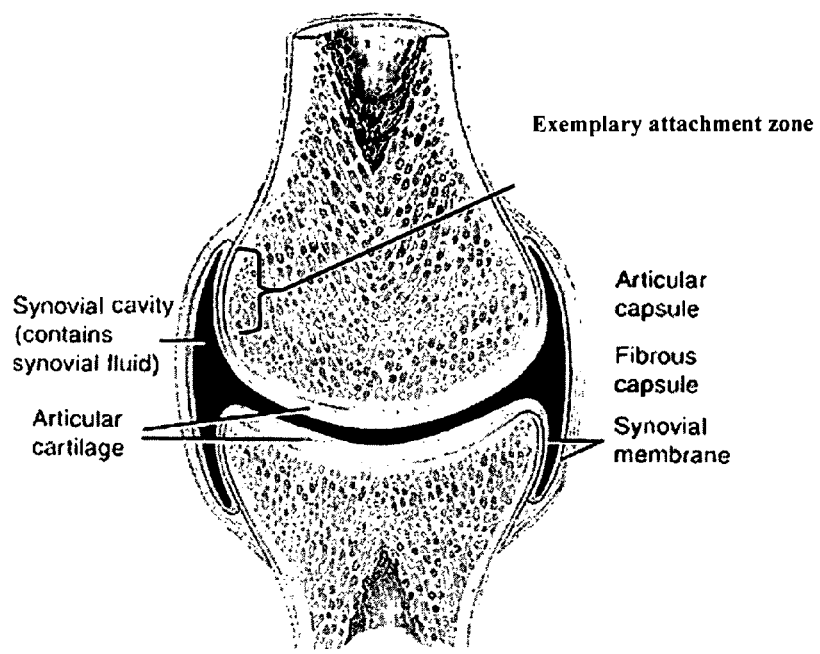
FIG. 3 depicts a cross section of a generalized synovial joint.

FIG. 3 shows one example of an attachment zone in a synovial joint. The joint depicted is an idealized synovial joint but roughly approximates the femur-tibia articulation at the knee. An exemplary attachment zone is indicated by the bracket. In this example, the indicated attachment zone is located in the joint and is remote from the load-bearing portions of the bone and also from the articulating surfaces of the bones. Although the zone may include portions of the bone with cartilage, the cartilage is not interfacing cartilage, i.e., does not form part of the articulation surface of the joint.

FIG. 4 shows exemplary placements of drug delivery devices in the depicted attachment zone. In accordance with the attachment zone example shown in FIG. 3, the device may be placed in a non-load-bearing and non-articulating portion of the bone. As suggested in FIG. 4, more than one device may be implanted in a single joint.

Figure 5:
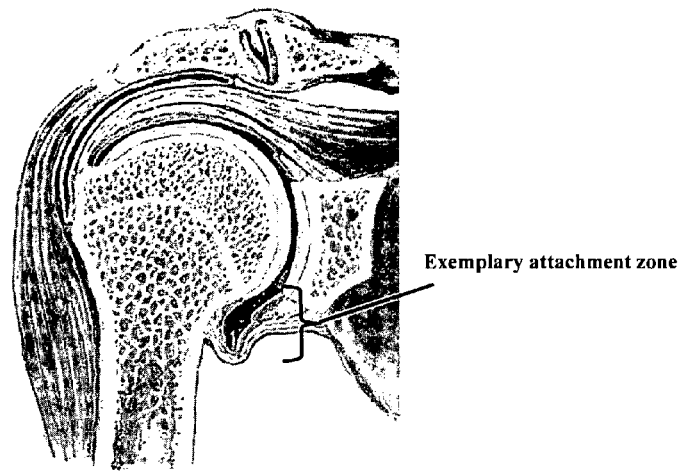
FIGS. 5-8 depict various synovial joints and exemplary placements of an intra-articular drug delivery device therein.
Figure 6:
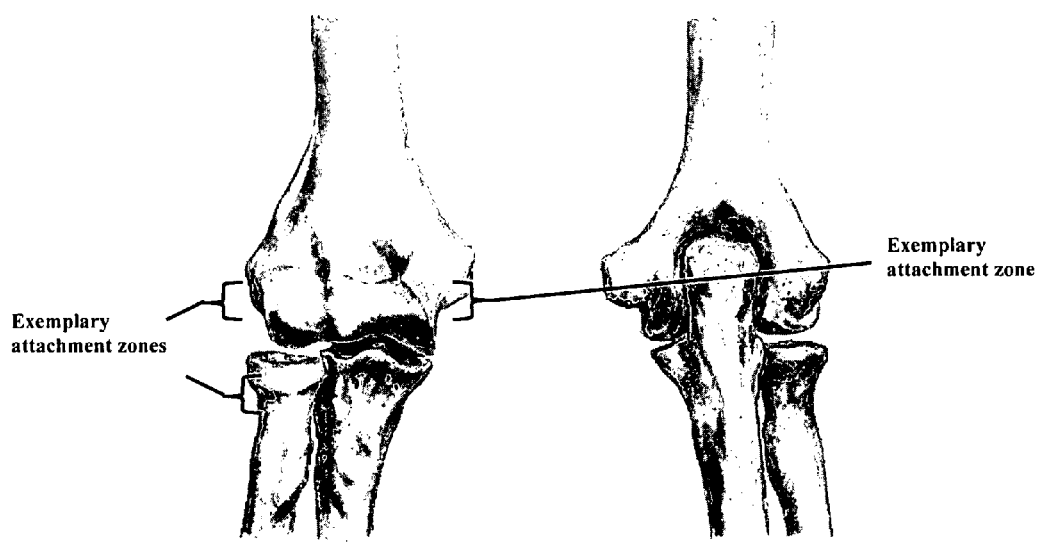
Figure 7:
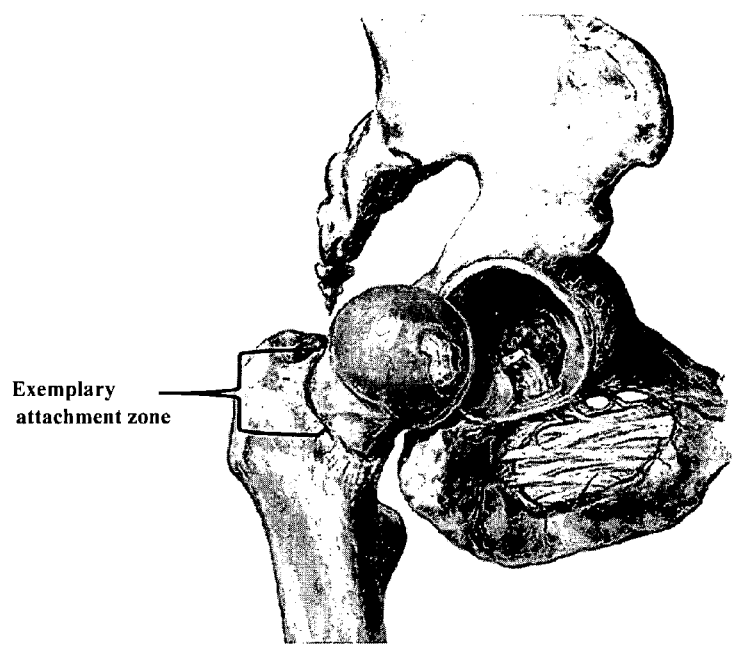
Figure 8:
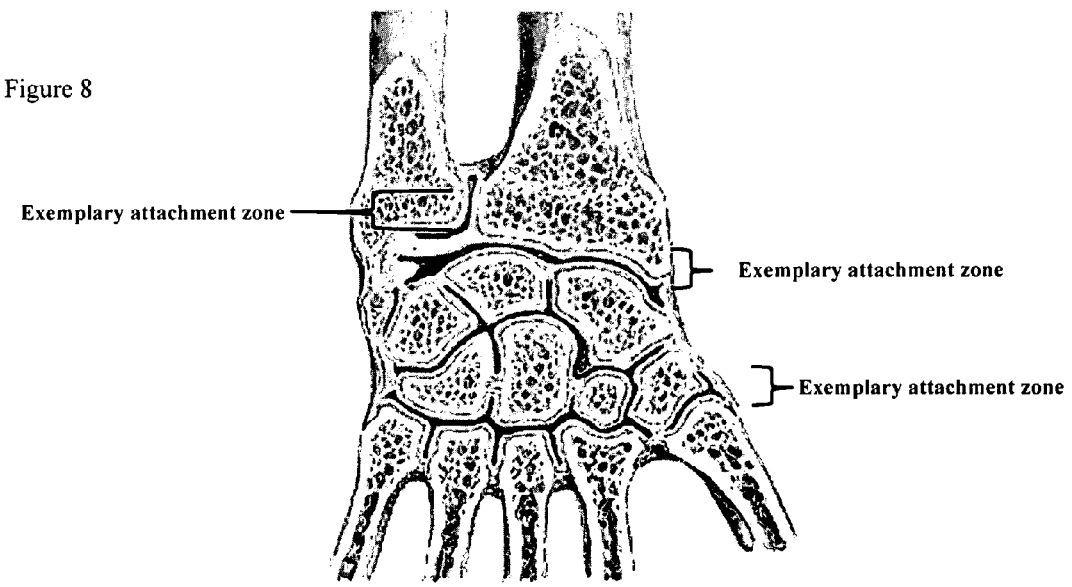

Attachment zones exist in every synovial joint. A joint may have more than one attachment zone, and attachment zones may noncontiguous (i.e., they may be regions of the joint isolated from each other). FIGS. 5-8 depict examples of attachment zones in the shoulder, elbow, hip, and wrist/thumb joints, respectively. As shown in FIG. 5, attachment zones in the shoulder joint can be in the area of redundant capsule medially and inferiorly. As shown in FIG. 6, attachment zones in the elbow can be at the distal aspect of the medial or lateral epicondyle superior to the trochlea and capitellum respectively, or just distal to the radial head on the neck of the radius. As shown in FIG. 7, a hip attachment zone exists just distal to the femoral head in the femoral neck. In FIG. 8, wrist and thumb (carpometacarpal) attachment zones are shown on the ulna at the distal aspect of the distal radioulnar joint, at the distal aspect of the radial styloid, and at the base of the first metacarpal. Other joints, such as various interfaces in the ankle, also have suitable attachment zones.

Figure 15:
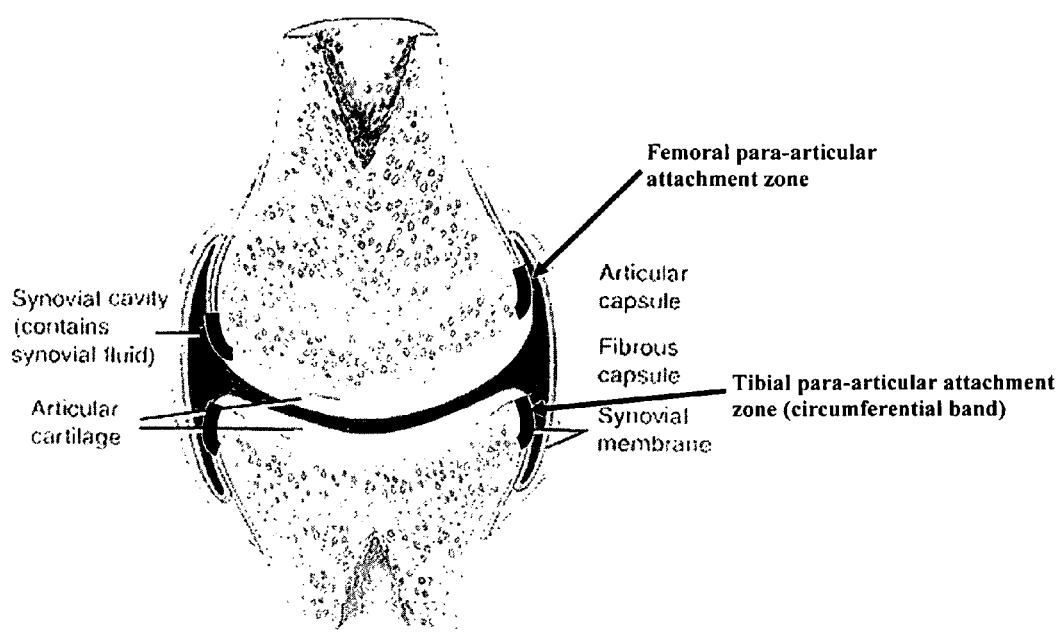
FIGS. 15-17 depict various synovial joints and exemplary placements of an intra-articular drug delivery device therein.
Figure 16:
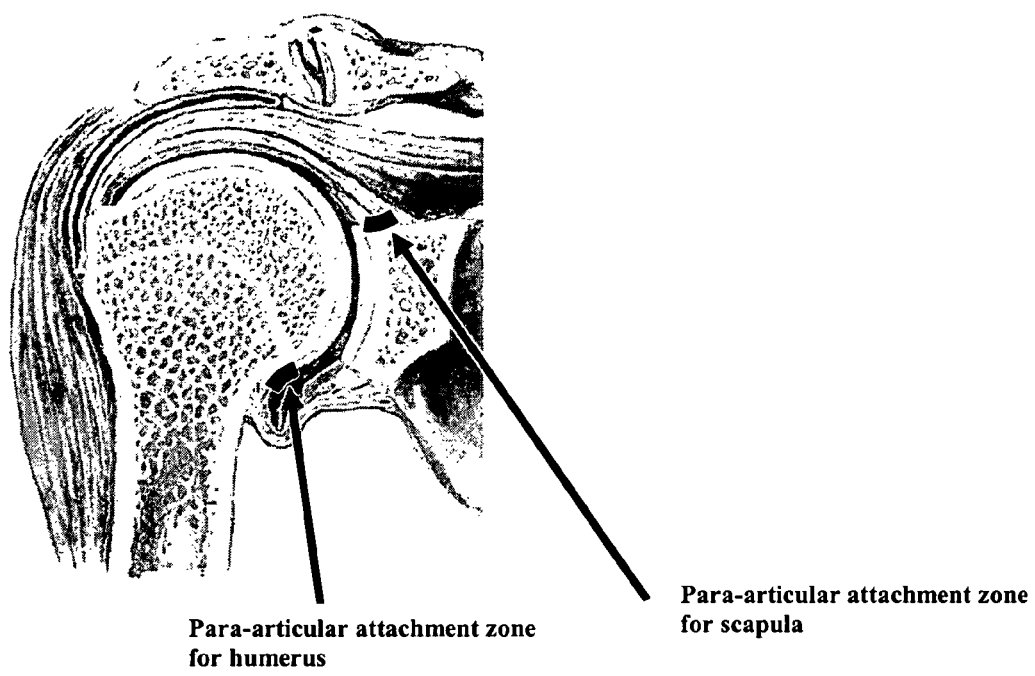
Figure 17:
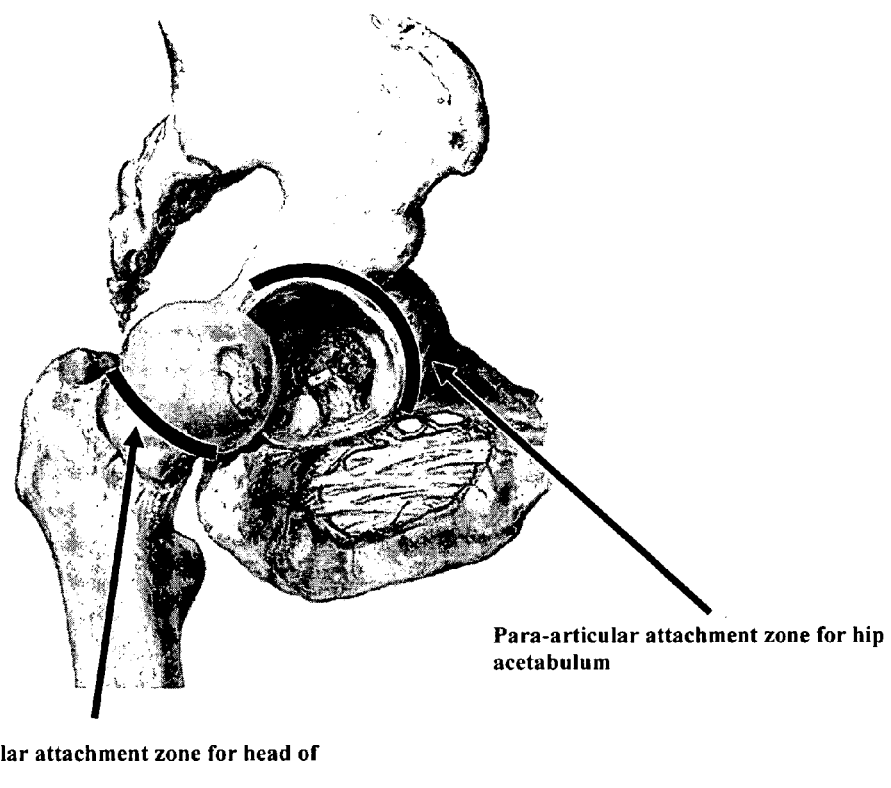

FIGS. 15-17 depict additional exemplary placements for drug delivery devices. The attachment zones indicated in the figures including nonarticulating regions of articular cartilage or bone. They may be said to be "para-articular" because they are located just outside the portions of articular cartilage that receive the articulating load. For example, FIG. 15, like FIG. 3, shows an idealized synovial joint that roughly approximates the knee articulation. The indicated attachment zones are identified as those portions of the articular cartilage that do not bear weight. Many synovial joints include articular cartilage that is non-load-bearing. A portion of non-load-bearing cartilage, then, can be removed in order to place a drug delivery device without harming the joint's load-bearing capacity, overall function, or health.

Portions of bone just beyond the non-load-bearing articulating cartilage can also be selected as attachment zones. An advantage of selecting an attachment zone illustrated in FIGS. 15-17 is that these attachment zones are as close as possible to the articulating surfaces of the joint without interfering with articulation. As a result, they are exposed to relatively robust synovial fluid circulation compared to the recesses of the joint where the synovial membrane folds back on itself. They are also more accessible by various surgical and minimally-invasive techniques for implantation, exchange, and/or removal. Another advantage is that regions of bone or cartilage nearer the articulation are less likely to become scarred or otherwise inaccessible following trauma or arthritic episodes in the joint.

Nonarticulating articular cartilage, as it might be called, can be found in the knee joint at both the tibial plateau and the femoral condyles, as well as in the patellofemoral area, the medial rim of the femoral trochlea, the lateral rim of the femoral trochlea, and the periphery of the intercondylar notch.

FIG. 16 depicts an exemplary shoulder joint and indicates some para-articular attachment zones. An attachment zone on the humerus may be found in a band just inferior to the anatomical neck, while an attachment zone on the scapula may be found around the ridge of the glenoid cavity or the glenoid neck.

FIG. 17 depicts an exemplary hip joint and indicates some para-articular attachment zones. An attachment zone on the femur is a band just inferior to the femoral head, while a para-articular attachment zone on the hip bone may be found in a band just around the rim of the acetabulum. This figure shows that articulating cartilage extends just past the margin of the acetabulum. The cartilage extending past the margin is para-articular because it does not touch the head of the femur and so does not bear a load.

Figure 18:
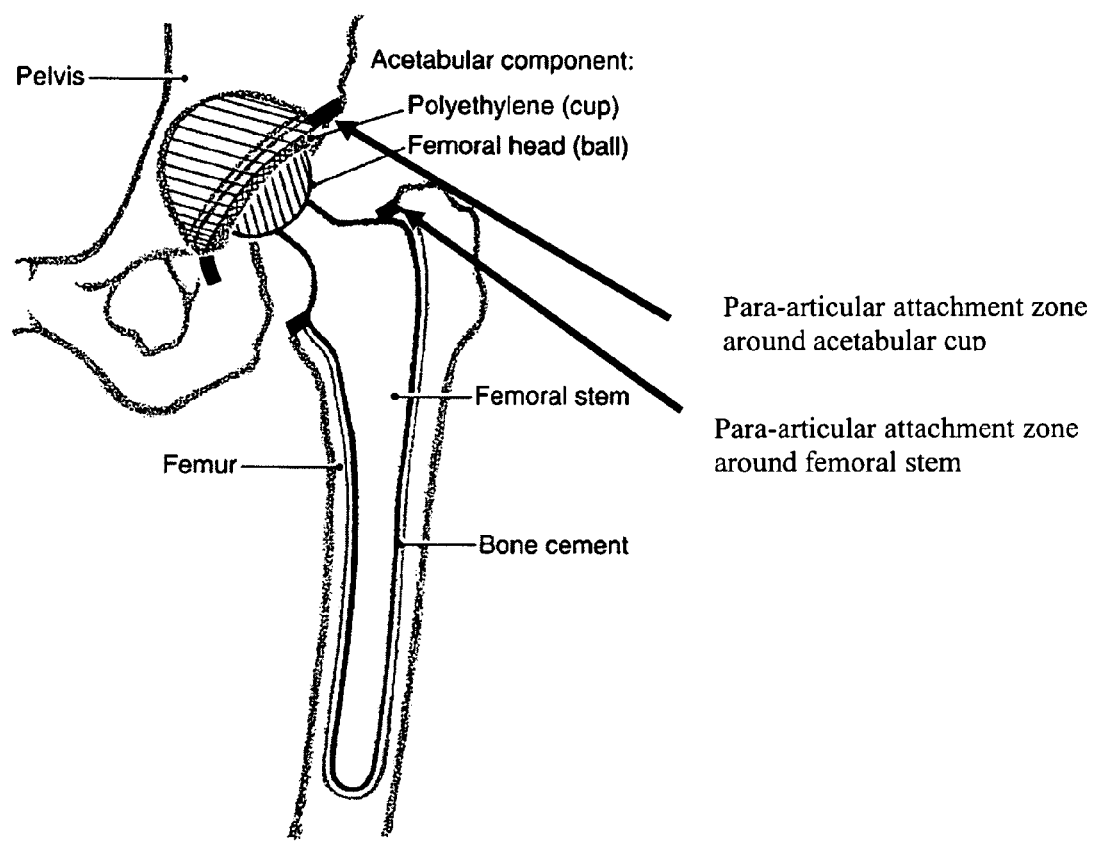
FIG. 18 depicts an exemplary placements of an intra-articular drug delivery device in the context of arthroplasty.

FIG. 18 depicts exemplary attachment zones in a joint that has been subjected to arthroplasty. When the natural para-articular cartilage and/or bone is removed, new attachment zones may be defined in non-articulating areas adjacent the prosthetic surfaces. As shown in FIG. 18 for a hip arthroplasty, attachments zones are defined as rims surrounding the prostheses. For example, a hip attachment zone is located in band adjacent the outer edge of the prosthetic acetabular cup, while a femoral attachment zone is located in a band around the prosthetic femoral stem. In an arthroplastic shoulder joint, attachment zones may be defined on the humerus as a band surrounding the humeral stem, and on the scapula in a band adjacent the outer edge of a glenoid component. In an arthroplastic knee, attachment zones may be defined on the femur as a band surrounding the femoral component of the knee replacement, and on the tibia as a band surrounding the tibial tray of the replacement.

When a bone is spared in an arthroplasty, the attachment zone may be defined as that of the native bone. In some cases, however, such a partial arthroplasty may change which portions of articulating cartilage bear weight. In that case, the para-articular attachment zone will be defined in a band around the articulating surface of the implant.

A drug delivery device may be implanted contemporaneously with arthroplasty. Benefits of contemporaneous fitting may be the forestalling, diminishing, or prevention of inflammation, infection, pain, etc., depending on which drugs are included in the drug delivery device. In one embodiment, a drug delivery device can be seated in the bone cement used to affix the prosthesis. Such seating would place the device in a very close but still para-articular position and would also eliminate the need for drilling a hole in bone.

The para-articular bands may vary widely in size and extent, depending on the joint and upon the anatomy and shape of the subject. A para-articular attachment zone may extend away from an articulating surface as much as about 1 cm, or as little as 5 mm, 4 mm, 3 mm, 2 mm, 1 mm, or about 0.5 mm.

An attachment zone can be selected in a variety of ways. In one embodiment, an image may be obtained of a bone or joint, such as a radiograph, a CT scan, an MRI, or other modality. The articulating surfaces can be identified by observing which portions of the subject bones are apposed. An attachment zone, such as one depicted in FIGS. 3-8, or a para-articular attachment zone, as depicted in FIGS. 15-18, may then be selected. The boundaries of a para-articular attachment zone can be identified by measuring an appropriate distance from the edge of an articulating surface. An attachment zone may be selected during arthroscopy or an open procedure by direct visualization of the articulating and non-articulating surfaces.

5. Therapeutic Agents

Possible biologically active agents include without limitation, medicaments; vitamins; mineral supplements; substances used for the treatment, prevention, diagnosis, cure or mitigation of disease or illness; or substances that affect the structure or function of the body.

The therapeutic agents are used in amounts that are therapeutically effective, which varies widely depending largely on the particular agent being used. The amount of agent incorporated into the composition also depends upon the desired release profile, the concentration of the agent required for a biological effect, and the length of time that the biologically active substance has to be released for treatment. In certain embodiments, the biologically active substance may be blended with a polymer matrix at different loading levels, in one embodiment at room temperature and without the need for an organic solvent. In other embodiments, the compositions may be formulated as microspheres.

There is no critical upper limit on the amount of therapeutic agent incorporated except for that of an acceptable solution or dispersion viscosity to maintain the physical characteristics desired for the composition. The lower limit of the agent incorporated into the polymer system is dependent upon the activity of the drug and the length of time needed for treatment. Thus, the amount of the agent should not be so small that it fails to produce the desired physiological effect, nor so large that the agent is released in an uncontrollable manner. Typically, within these limits, amounts of the therapeutic agents from about 1% up to about 60% may be incorporated into the present delivery systems. However, lesser amounts may be used to achieve efficacious levels of treatment for agent that are particularly potent.

Specific types of biologically active agents include, either directly or after appropriate modification, without limitation: anti-angiogenesis factors, antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antiproliferatives; antimitotics; antimetabolite compounds; angiostatics; angiostatic steroids; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; catecholamines; diuretics; vasodilators including general coronary, peripheral and cerebral; central nervous system stimulants; cough and cold preparations, including decongestants; growth factors, hormones such as estradiol and other steroids, including corticosteroids; hypnotics; immunosuppressives; steroids; corticosteroids; glucocorticoids; muscle relaxants; parasympatholytics; psychostimulants; sedatives; and tranquilizers; and naturally derived or genetically engineered proteins, polysaccharides, glycoproteins, lipoproteins, interferons, cytokines, chemotherapeutic agents and other anti-neoplastics, antibiotics, anti-virals, anti-fungals, anti-inflammatories, anticoagulants, lymphokines, or antigenic materials.

To illustrate further, other types of biologically active agents that may be used, either directly or after appropriate modification, include peptide, proteins or other biopolymers, e.g., interferons, interleukins, tumor necrosis factor, nerve growth factor (NGF), brain-derived neurotrophic factor (BDNF), neurotrophin-3 (NT-3), neurotrophin-4/5 (NT-4/5), ciliary neurotrophic factor (CNTF), glial cell line-derived neurotrophic factor (GDNF), cholinergic differentiation factor/Leukemia inhibitory factor (CDF/LIF), epidermal growth factor (EGF), insulin-like growth factor (IGF), basic fibroblast growth factor (bFGF), platelet-derived growth factor (PDGF), erythropoietin, growth hormone, Substance-P, neurotensin, insulin, erythropoietin, albumin, transferrin, and other protein biological response modifiers.

Other examples of biologically active agents that may be used either directly or after appropriate modification include acebutolol, acetaminophen, acetohydoxamic acid, acetophenazine, acyclovir, adrenocorticoids, allopurinol, alprazolam, aluminum hydroxide, amantadine, ambenonium, amiloride, aminobenzoate potassium, amobarbital, amoxicillin, amphetamine, ampicillin, androgens, anesthetics, anticoagulants, anticonvulsants-dione type, antithyroid medicine, appetite suppressants, aspirin, atenolol, atropine, azatadine, bacampicillin, baclofen, beclomethasone, belladonna, bendroflumethiazide, benzoyl peroxide, benzthiazide, benztropine, betamethasone, betha nechol, biperiden, bisacodyl, bromocriptine, bromodiphenhydramine, brompheniramine, buclizine, bumetamide, busulfan, butabarbital, butaperazine, caffeine, calcium carbonate, captopril, carbamazepine, carbenicillin, carbidopa & levodopa, carbinoxamine inhibitors, carbonic anhydsase, carisoprodol, carphenazine, cascara, cefaclor, cefadroxil, cephalexin, cephradine, chlophedianol, chloral hydrate, chlorambucil, chloramphenicol, chlordiazepoxide, chloroquine, chlorothiazide, chlorotrianisene, chlorpheniramine, 6× chlorpromazine, chlorpropamide, chlorprothixene, chlorthalidone, chlorzoxazone, cholestyramine, cimetidine, cinoxacin, clemastine, clidinium, clindamycin, clofibrate, clomiphere, clonidine, clorazepate, cloxacillin, colochicine, coloestipol, conjugated estrogen, contraceptives, cortisone, cromolyn, cyclacillin, cyclandelate, cyclizine, cyclobenzaprine, cyclophosphamide, cyclothiazide, cycrimine, cyproheptadine, danazol, danthron, dantrolene, dapsone, dextroamphetamine, dexamethasone, dexchlorpheniramine, dextromethorphan, diazepan, dicloxacillin, dicyclomine, diethylstilbestrol, diflunisal, digitalis, diltiazen, dimenhydrinate, dimethindene, diphenhydramine, diphenidol, diphenoxylate & atrophive, diphenylopyraline, dipyradamole, disopyramide, disulfiram, divalporex, docusate calcium, docusate potassium, docusate sodium, doxyloamine, dronabinol ephedrine, epinephrine, ergoloidmesylates, ergonovine, ergotamine, erythromycins, esterified estrogens, estradiol, estrogen, estrone, estropipute, etharynic acid, ethchlorvynol, ethinyl estradiol, ethopropazine, ethosaximide, ethotoin, fenoprofen, ferrous fumarate, ferrous gluconate, ferrous sulfate, flavoxate, flecainide, fluphenazine, fluprednisolone, flurazepam, folic acid, furosemide, gemfibrozil, glipizide, glyburide, glycopyrrolate, gold compounds, griseofuwin, guaifenesin, guanabenz, guanadrel, guanethidine, halazepam, haloperidol, hetacillin, hexobarbital, hydralazine, hydrochlorothiazide, hydrocortisone (cortisol), hydroflunethiazide, hydroxychloroquine, hydroxyzine, hyoscyamine, ibuprofen, indapamide, indomethacin, insulin, iofoquinol, iron-polysaccharide, isoetharine, isoniazid, isopropamide isoproterenol, isotretinoin, isoxsuprine, kaolin & pectin, ketoconazole, lactulose, levodopa, lincomycin liothyronine, liotrix, lithium, peramide, lorazepam, magnesium hydroxide, magnesium sulfate, magnesium trisilicate, maprotiline, meclizine, meclofenamate, medroxyproyesterone, melenamic acid, melphalan, mephenyloin, mephobarbital, methamate, mercaptopurine, mesoridazine, metaproterenol, metaxalone, methamphetamine, methaqualone, metharbital, methenamine, methicillin, methocarbamol, methotrexate, methsuximide, methyclothinzide, methylcellulos, methyldopa, methylergonovine, methylphenidate, methylprednisolone, methysergide, metoclopramide, metolazone, metoprolol, metronidazole, minoxidil, mitotane, monamine oxidase inhibitors, nadolol, nafcillin, nalidixic acid, naproxen, narcotic analgesics, neomycin, neostigmine, niacin, nicotine, nifedipine, nitrates, nitrofurantoin, nomifensine, norethindrone, norethindrone acetate, norgestrel, nylidrin, nystatin, orphenadrine, oxacillin, oxazepam, oxprenolol, oxymetazoline, oxyphenbutazone, pancrelipase, pantothenic acid, papaverine, para-aminosalicylic acid, paramethasone, paregoric, pemoline, penicillamine, penicillin, penicillin-v, pentobarbital, perphenazine, phenacetin, phenazopyridine, pheniramine, phenobarbital, phenolphthalein, phenprocoumon, phensuximide, phenylbutazone, phenylephrine, phenylpropanolamine, phenyl to loxamine, phenyloin, pilocarpine, pindolol, piper acetazine, piroxicam, poloxamer, polycarbophil calcium, polythiazide, potassium supplements, pruzepam, prazosin, prednisolone, prednisone, primidone, probenecid, probucol, procainamide, procarbazine, prochlorperazine, procyclidine, promazine, promethazine, propantheline, propranolol, pseudoephedrine, psoralens, psyllium, pyridostigmine, pyrodoxine, pyrilamine, pyrvinium, quinestrol, quinethazone, quinidine, quinine, ranitidine, rauwolfia alkaloids, riboflavin, rifampin, ritodrine, salicylates, scopolamine, secobarbital, senna, sannosides a & b, simethicone, sodium bicarbonate, sodium phosphate, sodium fluoride, spironolactone, sucrulfate, sulfacytine, sulfamethoxazole, sulfasalazine, sulfinpyrazone, sulfisoxazole, sulindac, talbutal, tamazepam, terbutaline, terfenadine, terphinhydrate, teracyclines, thiabendazole, thiamine, thioridazine, thiothixene, thyroblobulin, thyroid, thyroxine, ticarcillin, timolol, tocainide, tolazamide, tolbutamide, tolmetin trozodone, tretinoin, triamcinolone, trianterene, triazolam, trichlormethiazide, tricyclic antidepressants, tridhexethyl, trifluoperazine, triflupromazine, trihexyphenidyl, trimeprazine, trimethobenzamine, trimethoprim, tripclennamine, triprolidine, valproic acid, verapamil, vitamin A, vitamin B-12, vitamin C, vitamin D, vitamin E, vitamin K, xanthine, parathyroid hormone, enkephalins, and endorphins.

To illustrate further, antimetabolites may be used as upon appropriate modification if necessary, including without limitation methotrexate, 5-fluorouracil, cytosine arabinoside (ara-C), 5-azacytidine, 6-mercaptopurine, 6-thioguanine, and fludarabine phosphate. Antitumor antibiotics may include but are not limited to doxorubicin, daunorubicin, dactinomycin, bleomycin, mitomycin C, plicamycin, idarubicin, and mitoxantrone. Vinca alkaloids and epipodophyllotoxins may include, but are not limited to vincristine, vinblastine, vindesine, etoposide, and teniposide. Nitrosoureas, including carmustine, lomustine, semustine and streptozocin, may also be prodrugs, upon appropriate modification if necessary. Hormonal therapeutics may also be prodrugs, upon appropriate modification if necessary, such as corticosteriods (cortisone acetate, hydrocortisone, prednisone, prednisolone, methyl prednisolone dexamethasone, and fluocinolone acetonide), estrogens, (diethylstibesterol, estradiol, esterified estrogens, conjugated estrogen, chlorotiasnene), progestins (medroxyprogesterone acetate, hydroxy progesterone caproate, megestrol acetate), antiestrogens (tamoxifen), aromastase inhibitors (aminoglutethimide), androgens (testosterone propionate, methyltestosterone, fluoxymesterone, testolactone), antiandrogens (flutamide), LHRH analogues (leuprolide acetate), and endocrines for prostate cancer (ketoconazole). Antitumor drugs that are radiation enhancers may also be used as prodrugs, upon appropriate modification if necessary. Examples of such biologically active agents include, for example, the chemotherapeutic agents 5'-fluorouracil, mitomycin, cisplatin and its derivatives, taxol, bleomycins, daunomycins, and methamycins. Antibiotics may be used as prodrugs as well, upon appropriate modification if necessary, and they are well known to those of skill in the art, and include, for example, penicillins, cephalosporins, tetracyclines, ampicillin, aureothicin, bacitracin, chloramphenicol, cycloserine, erythromycin, gentamicin, gramacidins, kanamycins, neomycins, streptomycins, tobramycin, and vancomycin.

Other agents, upon appropriate modification if necessary, which may be used include those presently classified as investigational drugs, and can include, but are not limited to alkylating agents such as Nimustine AZQ, BZQ, cyclodisone, DADAG, CB10-227, CY233, DABIS maleate, EDMN, Fotemustine, Hepsulfam, Hexamethylmelamine, Mafosamide, MDMS, PCNU, Spiromustine, TA-077, TCNU and Temozolomide; antimetabolites, such as acivicin, Azacytidine, 5-azadeoxycytidine, A-TDA, Benzylidene glucose, Carbetimer, CB3717, Deazaguanine mesylate, DODOX, Doxifluridine, DUP-785, 10-EDAM, Fazarabine, Fludarabine, MZPES, MMPR, PALA, PLAC, TCAR, TMQ, TNC-P and Piritrexim; antitumor antibodies, such as AMPAS, BWA770U, BWA773U, BWA502U, Amonafide, m-AMSA, CI-921, Datelliptium, Mitonafide, Piroxantrone, Aclarubicin, Cytorhodin, Epirubicin, esorubicin, Idarubicin, Iodo-doxorubicin, Marcellomycin, Menaril, Morpholino anthracyclines, Pirarubicin, and SM-5887; microtubule spindle inhibitors, such as Amphethinile, Navelbine, and Taxol; the alkyl-lysophospholipids, such as BM41-440, ET-18-OCH3, and Hexacyclophosphocholine; metallic compounds, such as Gallium Nitrate, CL286558, CL287110, Cycloplatam, DWA2114R, NK121, Iproplatin, Oxaliplatin, Spiroplatin, Spirogermanium, and Titanium compounds; and novel compounds such as, for example, Aphidoicolin glycinate, Ambazone, BSO, Caracemide, DSG, Didemnin, B, DMFO, Elsamicin, Espertatrucin, Flavone acetic acid, HMBA, HHT, ICRF-187, Iododeoxyuridine, Ipomeanol, Liblomycin, Lonidamine, LY186641, MAP, MTQ, Merabarone SK&F104864, Suramin, Tallysomycin, Teniposide, THU and WR2721; and Toremifene, Trilosane, and zindoxifene.

6. Controlled-Release or Sustained Release Compositions

In certain aspects, controlled-release compositions, upon contact with synovial fluid, release the joint therapeutic over a sustained or extended period (as compared to the release from an isotonic saline solution). Such a system may result in prolonged delivery (over, for example, 2 to 4,000 hours, even 4 to 1500 hours) of effective amounts (e.g., 0.00001 mg/kg/hour to 10 mg/kg/hour) of the drug. This dosage form may be administered as is necessary depending on the subject being treated, the severity of the affliction, the judgment of the prescribing physician, and the like.

For treatment of joints, controlled-release compositions are adapted for application to the joint. As used herein, the term "anatomic area" refers to an area of synovial joint anatomy, i.e., a joint that facilitates movement of the bones it articulates. In certain embodiments, the pharmaceutical compositions are understood to exert their effect in part by contact with a portion of the anatomic area being treated. Contact refers to a physical touching, either directly with the subject composition being applied without intervening barrier to the anatomic area being treated, or indirectly, where the subject composition is applied to or is formed on a surface of an interposed material, passing through to come into direct contact with the anatomic area being treated. Contact, as used herein, includes those situations where the pharmaceutical compounds are initially positioned to contact the anatomic area being treated, and those situations where the controlled-release compositions are initially positioned in proximity to the anatomic area being treated without contacting it, and subsequently move, migrate, flow, spread, or are transported to enter into contact with the anatomic area being treated.

Contact may include partial contacts, wherein the pharmaceutical compounds only contact a portion of the anatomic area being treated, or the edge or periphery or margin of the anatomic area being treated. Contact of the pharmaceutical compounds with the anatomic area being treated occurs from a local rather than systemic administration of said compounds, as these terms are defined hereinafter. The composition may be formed as a flowable material, insertable into the anatomic area. A variety of devices and methods for inserting the composition into the preselected anatomic area will be familiar to practitioners of ordinary skill in the art, for example infusion, injection, topical application, spraying, painting, coating, formed gel placement, and others. The composition, alternatively, may be formed as a solid object implantable in the anatomic area, or as a film or mesh that may be used to cover a segment of the area. A variety of techniques for implanting solid objects in relevant anatomic areas will be likewise familiar to practitioners of ordinary skill in the art.

Some examples of sustained release devices and compositions are described in U.S. Pat. Nos. 5,618,563, 5,792,753, 5,942,241, 5,985,850, 6,096,728, 6,214,387, 6,217,911, 6,248,345, 6,335,035, 6,346,519, 6,426,339, 6,428,804, 6,451,335, 6,511,958, 6,514,514, 6,514,516, 6,521,259, 6,524,606, 6,524,607, 6,527,760, 6,528,097, 6,528,107, 6,534,081, 6,565,534, 6,582,715, 6,590,059, and 6,699,471; and in U.S. Patent Application Publication Nos. U.S. 2003/0139811 A1 and U.S. 2003/0093157 A1; and in PCT Publication No. WO/0061152 A1. All of these documents are hereby incorporated herein by this reference.

In some embodiments, the polymer composition may be a flexible or flowable material. When the polymer used is itself flowable, the polymer composition, even when viscous, need not include a biocompatible solvent to be flowable, although trace or residual amounts of biocompatible solvents may still be present.

In certain embodiments, a fluid polymer may be especially suitable for the treatment of joint problems. A fluid material may be adapted for injection or instillation into a tissue mass or into an actual or potential space. Certain types of fluid polymers may be termed flowable. A flowable material, often capable of assuming the shape of the contours of an irregular space, may be delivered to a portion of an actual or potential space to flow therefrom into a larger portion of the space. In this way, the flowable material may come to coat an entire post-operative surgical site after being inserted through an edge of an incision or after being instilled through a drain or catheter left in the surgical bed. Alternatively, if the flowable material is inserted under pressure through a device such as a needle or a catheter, it may perform hydrodissection, thus opening up a potential space and simultaneously coating the space with polymer. Such potential spaces suitable for hydrodissection may be found in various identifiable anatomic areas in joints. A flowable polymer may be particularly adapted for instillation through a needle, catheter or other delivery device such as an endoscope, since its flowable characteristics allow it to reach surfaces that extend beyond the immediate reach of the delivery device. A flowable polymer in a highly fluid state may be suitable for injection through needles or catheters into tissue masses, such as tumors or margins of resection sites. Physical properties of polymers may be adjusted to achieve a desirable state of fluidity or flowability by modification of their chemical components and crosslinking, using methods familiar to practitioners of ordinary skill in the art.

A flexible polymer may be used in the fabrication of a solid article. Flexibility involves having the capacity to be repeatedly bent and restored to its original shape. Solid articles made from flexible polymers are adapted for placement in anatomic areas where they will encounter the motion of adjacent organs or body walls. Certain areas of motion are familiar to practitioners dealing with joint problems. A flexible solid article can thus be sufficiently deformed by those moving tissues that it does not cause tissue damage. Flexibility is particularly advantageous where a solid article might be dislodged from its original position and thereby encounter an unanticipated moving structure; flexibility may allow the solid article to bend out of the way of the moving structure instead of injuring it. Solid articles may be formed as films, meshes, sheets, tubes, or any other shape appropriate to the dimensions and functional requirements of the particular anatomic area. Physical properties of polymers may be adjusted to attain a desirable degree of flexibility by modification of the chemical components and crosslinking thereof, using methods familiar to practitioners of ordinary skill in the art.

While it is possible that the biocompatible polymer or the biologically active agent may be dissolved in a small quantity of a solvent that is non-toxic to more efficiently produce an amorphous, monolithic distribution or a fine dispersion of the biologically active agent in the flexible or flowable composition, it is an advantage that, in an embodiment, no solvent is needed to form a flowable composition. Moreover, the use of solvents may be avoided because, once a polymer composition containing solvent is placed totally or partially within the body, the solvent dissipates or diffuses away from the polymer and must be processed and eliminated by the body, placing an extra burden on the body's clearance ability at a time when the illness (and/or other treatments for the illness) may have already deleteriously affected it.

However, when a solvent is used to facilitate mixing or to maintain the flowability of the polymer composition, it should be non-toxic, otherwise biocompatible, and should be used in relatively small amounts. Solvents that are toxic clearly should not be used in any material to be placed even partially within a living body. Such a solvent also must not cause substantial tissue irritation or necrosis at the site of administration.

Examples of suitable biocompatible solvents, when used, include N-methyl-2-pyrrolidone, 2-pyrrolidone, ethanol, propylene glycol, acetone, methyl acetate, ethyl acetate, methyl ethyl ketone, dimethylformamide, dimethyl sulfoxide, tetrahydrofuran, caprolactam, dimethyl-sulfoxide, oleic acid, or 1-dodecylazacycloheptan-2-one. In one embodiment, solvents include N-methyl-2-pyrrolidone, 2-pyrrolidone, dimethyl sulfoxide, and acetone because of their solvating ability and their biocompatibility.

The microspheres may be manufactured by incorporating the drug into the polymer matrix by either dissolving or suspending the drug into polymer solution and the mixture will be subsequently dried by techniques familiar to those skill in the arts to form microspheres. These techniques include but not limited to spray drying, coating, various emulsion methods and supercritical fluid processing. The microspheres may be mixed with a pharmaceutically acceptable diluent prior to the administration for injection. They may also be directly applied to the desired site, such as a surgical wound or cavity, by various delivery systems including pouring and spraying. The microspheres may also be mixed with pharmaceutically acceptable ingredients to create ointment or cream for topical applications.

In certain embodiments, the subject polymers are soluble in one or more common organic solvents for ease of fabrication and processing. Common organic solvents include such solvents as chloroform, dichloromethane, dichloroethane, 2-butanone, butyl acetate, ethyl butyrate, acetone, ethyl acetate, dimethylacetamide, N-methylpyrrolidone, dimethylformamide, and dimethylsulfoxide.

In addition, the polymer compositions may comprise blends of the polymer with other biocompatible polymers or copolymers, so long as the additional polymers or copolymers do not interfere undesirably with the biocompatible, biodegradable and/or mechanical characteristics of the composition. Blends of the polymer with such other polymers may offer even greater flexibility in designing the precise release profile desired for targeted drug delivery or the precise rate of biodegradability desired. Examples of such additional biocompatible polymers include other poly(phosphoesters), poly(carbonates), poly(esters), poly(orthoesters), poly (amides), poly(urethanes), poly(imino-carbonates), and poly (anhydrides).

Pharmaceutically acceptable polymeric carriers may also comprise a wide range of additional materials. Without being limited thereto, such materials may include diluents, binders and adhesives, lubricants, disintegrants, colorants, bulking agents, flavorings, sweeteners, and miscellaneous materials such as buffers and adsorbents, in order to prepare a particular medicated composition, with the condition that none of these additional materials will interfere with the intended purpose of the subject composition.

Plasticizers and stabilizing agents known in the art may be incorporated in polymers. In certain embodiments, additives such as plasticizers and stabilizing agents are selected for their biocompatibility.

A composition may further contain one or more adjuvant substances, such as fillers, thickening agents or the like. In other embodiments, materials that serve as adjuvants may be associated with the polymer matrix. Such additional materials may affect the characteristics of the polymer matrix that results. For example, fillers, such as bovine serum albumin (BSA) or mouse serum albumin (MSA), may be associated with the polymer matrix. In certain embodiments, the amount of filler may range from about 0.1 to about 50% or more by weight of the polymer matrix, or about 2.5, 5, 10, 25, 40 percent. Incorporation of such fillers may affect the biodegradation of the polymeric material and/or the sustained release rate of any encapsulated substance. Other fillers known to those of skill in the art, such as carbohydrates, sugars, starches, saccharides, celluoses and polysaccharides, including mannitose and sucrose, may be used in certain embodiments.

In other embodiments, spheronization enhancers facilitate the production of subject polymeric matrices that are generally spherical in shape. Substances such as zein, microcrystalline cellulose or microcrystalline cellulose co-processed with sodium carboxymethyl cellulose may confer plasticity to the subject compositions as well as implant strength and integrity. In particular embodiments, during spheronization, extrudates that are rigid, but not plastic, result in the formation of dumbbell shaped implants and/or a high proportion of fines, and extrudates that are plastic, but not rigid, tend to agglomerate and form excessively large implants. In such embodiments, a balance between rigidity and plasticity is desirable. The percent of spheronization enhancer in a formulation depends on the other excipient characteristics and is typically in the range of 10-90% (w/w).

Buffers, acids and bases may be incorporated in the subject compositions to adjust their pH. Agents to increase the diffusion distance of agents released from the polymer matrix may also be included.

Disintegrants are substances which, in the presence of liquid, promote the disruption of the subject compositions. Disintegrants are most often used in implants, in which the function of the disintegrant is to counteract or neutralize the effect of any binding materials used in the subject formulation. In general, the mechanism of disintegration involves moisture absorption and swelling by an insoluble material. Examples of disintegrants include croscarmellose sodium and crospovidone that, in certain embodiments, may be incorporated into the polymeric matrices in the range of about 1-20% of total matrix weight. In other cases, soluble fillers such as sugars (mannitol and lactose) may also be added to facilitate disintegration of the subject compositions upon use.

Other materials may be used to advantage to control the desired release rate of a therapeutic agent for a particular treatment protocol. For example, if the sustained release is too slow for a particular application, a pore-forming agent may be added to generate additional pores in the matrix. Any biocompatible water-soluble material may be used as the pore-forming agent. They may be capable of dissolving, diffusing or dispersing out of the formed polymer system whereupon pores and microporous channels are generated in the system. The amount of pore-forming agent (and size of dispersed particles of such pore-forming agent, if appropriate) within the composition should affect the size and number of the pores in the polymer system.

Pore-forming agents include any pharmaceutically acceptable organic or inorganic substance that is substantially miscible in water and body fluids and will dissipate from the forming and formed matrix into aqueous medium or body fluids or water-immiscible substances that rapidly degrade to water-soluble substances. Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and polyvinylpyrrolidone. The size and extent of the pores may be varied over a wide range by changing the molecular weight and percentage of pore-forming agent incorporated into the polymer system.

The charge, lipophilicity or hydrophilicity of any subject polymeric matrix may be modified by attaching in some fashion an appropriate compound to the surface of the matrix. For example, surfactants may be used to enhance wettability of poorly soluble or hydrophobic compositions. Examples of suitable surfactants include dextran, polysorbates and sodium lauryl sulfate. In general, surfactants are used in low concentrations, generally less than about 5%.

Binders are adhesive materials that may be incorporated in polymeric formulations to bind and maintain matrix integrity. Binders may be added as dry powder or as solution. Sugars and natural and synthetic polymers may act as binders. Materials added specifically as binders are generally included in the range of about 0.5%-15% w/w of the matrix formulation. Certain materials, such as microcrystalline cellulose, also used as a spheronization enhancer, also have additional binding properties.

Various coatings may be applied to modify the properties of the matrices. Three exemplary types of coatings are seal, gloss and enteric coatings. Other types of coatings having various dissolution or erosion properties may be used to further modify subject matrices behavior, and such coatings are readily known to one of ordinary skill in the art.

The seal coat may prevent excess moisture uptake by the matrices during the application of aqueous based enteric coatings. The gloss coat generally improves the handling of the finished matrices. Water-soluble materials such as hydroxypropyl cellulose may be used to seal coat and gloss coat implants. The seal coat and gloss coat are generally sprayed onto the matrices until an increase in weight between about 0.5% and about 5%, often about 1% for a seal coat and about 3% for a gloss coat, has been obtained.

Enteric coatings consist of polymers which are insoluble in the low pH (less than 3.0) of the stomach, but are soluble in the elevated pH (greater than 4.0) of the small intestine. Polymers such as EUDRAGIT, Rohm Tech, Inc., Malden, Mass., and AQUATERIC, FMC Corp., Philadelphia, Pa., may be used and are layered as thin membranes onto the implants from aqueous solution or suspension or by a spray drying method. The enteric coat is generally sprayed to a weight increase of about one to about 30%, or about 10 to about 15% and may contain coating adjuvants such as plasticizers, surfactants, separating agents that reduce the tackiness of the implants during coating, and coating permeability adjusters.

The present compositions may additionally contain one or more optional additives such as fibrous reinforcement, colorants, perfumes, rubber modifiers, modifying agents, etc. In practice, each of these optional additives should be compatible with the resulting polymer and its intended use. Examples of suitable fibrous reinforcement include PGA microfibrils, collagen microfibrils, cellulosic microfibrils, and olefinic microfibrils. The amount of each of these optional additives employed in the composition is an amount necessary to achieve the desired effect.

The subject polymers may be formed in a variety of shapes. For example, in certain embodiments, subject polymer matrices may be presented in the form of microparticles or nanoparticles. Such particles may be prepared by a variety of methods known in the art, including for example, solvent evaporation, spray-drying or double emulsion methods.

The shape of microparticles and nanoparticles may be determined by scanning electron microscopy. Spherically shaped nanoparticles are used in certain embodiments for circulation through the bloodstream. If desired, the particles may be fabricated using known techniques into other shapes that are more useful for a specific application.

In addition to intracellular delivery of a therapeutic agent, it also possible that particles of the subject compositions, such as microparticles or nanoparticles, may undergo endocytosis, thereby obtaining access to the cell. The frequency of such an endocytosis process will likely depend on the size of any particle.

In certain embodiments, solid articles useful in defining shape and providing rigidity and structural strength to the polymeric matrices may be used. For example, a polymer may be formed on a mesh or other weave for implantation. A polymer may also be fabricated as a stent or as a shunt, adapted for holding open areas within body tissues or for draining fluid from one body cavity or body lumen into another. Further, a polymer may be fabricated as a drain or a tube suitable for removing fluid from a post-operative site, and in some embodiments adaptable for use with closed section drainage systems such as Jackson-Pratt drains and the like familiar in the art.

The mechanical properties of the polymer may be important for the processability of making molded or pressed articles for implantation. For example, the glass transition temperature may vary widely but must be sufficiently lower than the temperature of decomposition to accommodate conventional fabrication techniques, such as compression molding, extrusion or injection molding.

In certain embodiments, the polymers and blends, upon contact with body fluids, undergo gradual degradation. The life of a biodegradable polymer in vivo depends, among other things, upon its molecular weight, crystallinity, biostability, and the degree of crosslinking. In general, the greater the molecular weight, the higher the degree of crystallinity, and the greater the biostability, the slower biodegradation will be.

If a subject polymer matrix is formulated with a therapeutic agent, release of such an agent for a sustained or extended period as compared to the release from an isotonic saline solution generally results. Such release profile may result in prolonged delivery (over, say 1 to about 4,000 hours, or alternatively about 4 to about 1500 hours) of effective amounts (e.g., about 0.00001 mg/kg/hour to about 10 mg/kg/hour) of the agent associated with the polymer.

A variety of factors may affect the desired rate of hydrolysis of polymers, the desired softness and flexibility of the resulting solid matrix, rate and extent of bioactive material release. Some of such factors include: the selection of the various substituent groups, such as the phosphate group making up the linkage in the polymer backbone (or analogs thereof), the enantiomeric or diastereomeric purity of the monomeric subunits, homogeneity of subunits found in the polymer, and the length of the polymer. For instance, the present disclosure contemplates heteropolymers with varying linkages, and/or the inclusion of other monomeric elements in the polymer, in order to control, for example, the rate of biodegradation of the matrix.

To illustrate further, a wide range of degradation rates may be obtained by adjusting the hydrophobicities of the backbones or side chains of the polymers while still maintaining sufficient biodegradability for the use intended for any such polymer. Such a result may be achieved by varying the various functional groups of the polymer. For example, the combination of a hydrophobic backbone and a hydrophilic linkage produces heterogeneous degradation because cleavage is encouraged whereas water penetration is resisted. In another example, it is expected that use of substituent on phosphate in the polymers that is lipophilic, hydrophobic or bulky group would slow the rate of degradation. For example, it is expected that conversion of the phosphate side chain to a more lipophilic, more hydrophobic or more sterically bulky group would slow down the rate of biodegradation. Thus, release is usually faster from polymer compositions with a small aliphatic group side chain than with a bulky aromatic side chain.

One protocol generally accepted in the field that may be used to determine the release rate of any therapeutic agent or other material loaded in the polymer matrices involves degradation of any such matrix in a 0.1 M PBS solution (pH 7.4) at 37° C., an assay known in the art. For purposes of the present disclosure, the term "PBS protocol" is used herein to refer to such protocol.

In certain instances, the release rates of different polymer systems may be compared by subjecting them to such a protocol. In certain instances, it may be necessary to process polymeric systems in the same fashion to allow direct and relatively accurate comparisons of different systems to be made. Such comparisons may indicate that any one polymeric system releases incorporated material at a rate from about 2 or less to about 1000 or more times faster than another polymeric system. Alternatively, a comparison may reveal a rate difference of about 3, 5, 7, 10, 25, 50, 100, 250, 500 or 750. Even higher rate differences are contemplated by the present disclosure and release rate protocols.

In certain embodiments, when formulated in a certain manner, the release rate for polymer systems may present as mono- or bi-phasic. Release of any material incorporated into the polymer matrix, which is often provided as a microsphere, may be characterized in certain instances by an initial increased release rate, which may release from about 5 to about 50% or more of any incorporated material, or alternatively about 10, 15, 20, 25, 30 or 40%, followed by a release rate of lesser magnitude.

The release rate of any incorporated material may also be characterized by the amount of such material released per day per mg of polymer matrix. For example, in certain embodiments, the release rate may vary from about 1 ng or less of any incorporated material per day per mg of polymeric system to about 5000 or more ng/day.mg. Alternatively, the release rate may be about 10, 25, 50, 75, 100, 125, 150, 175, 200, 250, 300, 350, 400, 450, 500, 600, 700, 800 or 900 ng/day.mg. In still other embodiments, the release rate of any incorporated material may be 10,000 ng/day.mg or even higher. In certain instances, materials incorporated and characterized by such release rate protocols may include therapeutic agents, fillers, and other substances.

In another aspect, the rate of release of any material from any polymer matrix may be presented as the half-life of such material in the such matrix.

In addition to the embodiment involving protocols for in vitro determination of release rates, in vivo protocols, whereby in certain instances release rates for polymeric systems may be determined in vivo, are also contemplated by the present disclosure. Other assays useful for determining the release of any material from the polymers of the present system are known in the art.

7. Combinations of Controlled-Release Composition and Therapeutic Agent

In some embodiments, for delivery of a therapeutic agent, the agent is added to the polymer composition. A variety of methods are known in the art for encapsulating a biologically active substance in a polymer. For example, the agent or substance may be dissolved to form a homogeneous solution of reasonably constant concentration in the polymer composition, or it may be dispersed to form a suspension or dispersion within the polymer composition at a desired level of "loading" (grams of biologically active substance per grams of total composition including the biologically active substance, usually expressed as a percentage).

In part, a polymer composition useful in the treatment of joint pain, inflammation, infection, or other problems, includes both: (a) a therapeutic agent, and (b) a biocompatible and optionally biodegradable polymer, such as one having the recurring monomeric units shown in one of the foregoing formulas, or any other biocompatible polymer mentioned above or known in the art. In certain embodiments in which the subject composition will be used to treat pain, the agent is an analgesic or anesthetic; for inflammation, a steroidal or non-steroidal antiinflammatory agent; and for infection, an antimicrobial effective against the pathogen(s) of concern, such as an antibiotic, antifungal, antimycotic, antimalarial, antimycobacterial, antiparasitic, or antiviral. In some embodiments, the subject compositions encapsulate more than one agent for treatment of one or more joint problems.

8. Delivery Systems

In its simplest form, a delivery system for a therapeutic agent for treatment of a joint problem consists of a dispersion of such an agent into one of the polymers described above. In other embodiments, an article is used for implantation, injection, or otherwise placed totally or partially within the body, the article comprising a composition for treatment of a joint problem. It may be particularly important that such an article result in minimal tissue irritation when applied to, implanted in or injected into vascularized tissue, hypovascularized postoperative tissue or tissue exposed to previous radiation that is part of a joint. In certain embodiments, a solid, flowable or fluid article is inserted within an anatomic area by implantation, injection, endoscopy or otherwise being placed within an anatomic area of the subject being treated for a joint problem.

As a structural medical device, the polymer compositions provide a wide variety of physical forms having specific chemical, physical and mechanical properties suitable for insertion into an anatomic area.

Biocompatible delivery systems and articles thereof, may be prepared in a variety of ways known in the art. The subject polymer may be melt processed using conventional extrusion or injection molding techniques, or these products may be prepared by dissolving in an appropriate solvent, followed by formation of the device, and subsequent removal of the solvent by evaporation or extraction, e.g., by spray drying. By these methods, the polymers may be formed into articles of almost any size or shape desired, for example, implantable solid discs or wafers or injectable rods, microspheres, or other microparticles. Typical medical articles also include such as implants as laminates for degradable fabric or coatings to be placed on other implant devices.

In one embodiment, certain polymer compositions may be used to form a soft, drug-delivery "depot" that can be administered as a liquid, for example, by injection, but which remains sufficiently viscous to maintain the drug within the localized area around the injection site. By using a polymer composition in flowable form, even the need to make an incision can be eliminated. In any event, the flexible or flowable delivery "depot" will adjust to the shape of the space it occupies within the body with a minimum of trauma to surrounding tissues.

When the polymer composition is flexible or flowable, it may be placed anywhere within the body, including into an anatomic area of a joint. It may be inserted into the anatomic area either through an open surgical wound, under direct or indirect vision, or through any of the access devices routinely used in the art to enter such areas, for example, indwelling or acutely-inserted catheters, needles, drains, superselective angiography means and the like. A flowable or fluid polymer may be adapted for mixing with the transudate or exudate found within or expected to gather within the anatomic area. A flowable or fluid polymer may be instilled in an anatomic area during surgery on organs or structures therein to decrease the likelihood of recurrent disease when there is a high risk for its development. In certain embodiments, a polymer composition may also be incorporated in access devices so that a therapeutic agent is released into the anatomic area within which the access device resides. The polymer composition may also be used to produce coatings for other solid implantable devices for treatment of joint problems.

Once a system or implant article is in place, it should remain in at least partial contact with a biological fluid, such as blood, tissue fluid, lymph, or secretions from organ surfaces or mucous membranes, and the like to allow for sustained release of any encapsulated therapeutic agent, e.g., a therapeutic agent.

These examples of the clinical utility of the disclosed devices and methods have been provided for illustrative purposes only. Other exemplary utilizations will be apparent to practitioners of ordinary skill in the art using no more than routine experimentation.

EXAMPLES

Example 1

In one example, the drug carrier is provided as a cartridge. The drug may be loaded into the cartridge as a powder, compressed solid, or as granules without a polymer mixture. Alternative the drug may be combined with any suitable biocompatible, biodegradable polymer. Examples of such biocompatible biodegradable polymers useful include: hydroxyaliphatic carboxylic acids, either homo- or copolymers, such as polylactic acid, polyglycolic acid, polylactic glycolic acid; polysaccharides such as cellulose or cellulose derivatives such as ethyl cellulose, cross-linked or uncross-linked sodium carboxymethyl cellulose, sodium carboxymethylcellulose starch, cellulose ethers, cellulose esters such as cellulose acetate, cellulose acetate phthallate, hydroxypropylmethyl cellulose phthallate and calcium alginate, polypropylene, polybutyrates, polycarbonate, acrylate polymers such as polymethacrylates, polyanhydrides, polyvalerates, polycaprolactones such as poly-.epsilon.-caprolactone, polydimethylsiloxane, polyamides, polyvinylpyrollidone, polyvinylalcohol phthallate, waxes such as paraffin wax and white beeswax, natural oils, shellac, zein, hyaluronic acid, or a mixture thereof.

Example 2

In one exemplary embodiment, a sustained release device includes a polymeric matrix or liposome from which drug is released by diffusion and/or degradation of the matrix. The release pattern is usually principally determined by the matrix material, as well as by the percent loading, method of manufacture, type of drug being administered and type of device, for example, microsphere. A major advantage of a biodegradable controlled release system over others is that it does not require the surgical removal of the drug depleted device, which is slowly degraded and absorbed by the patient's body, and ultimately cleared along with other soluble metabolic waste products.

Systemic anesthetics such as methoxyflurane, have been incorporated into liposomes and lecithin microdroplets, for example, as described by Haynes, et al., Anesthesiology 63:490-499 (1985). To date, the liposome and lecithin preparations have not been widely applied in clinical or laboratory practice, because of their inability to provide dense blockade for a prolonged period of time (i.e., three or more days) in a safe and controlled manner. The lecithin microdroplets and liposomes degrade or are phagocytized too rapidly, in a matter of hours. Other lipid based devices, formed in combination with polymer, for release of local anesthetics are described by U.S. Pat. No. 5,188,837 to Domb. Researchers have also explored the use of polymer microspheres constructed of poly-lactic-glycolic acid combinations for the release of local anesthetics and antiinflammtories such as bupivicaine and dexamethasone with some initial promise in nerve blockade (Drager et. al., Anesthesiology 89(4):969-979 (1998)).

Example 3

A biocompatible intra-articular device size for implantation within a joint to continuously deliver a drug within the joint for a period of at least several weeks may include an outer bone anchor construct and an inner core consisting of a drug/polymer reservoir. The drug/polymer reservoir elutes a drug that dissolves in joint fluid through a semipermeable membrane at the synovial fluid interface. The device is implanted in a non-loaded but intra-articular portion of the joint where synovial fluid agitation across the semi-permeable membrane promotes drug elution.

Example 4

Exemplary sustained release compositions include polyglycolic acid, polylactic acid, polyester, collagen, a hydrogel, hyaluronic acid, and combinations of these.

Example 5

Exemplary therapeutic agents include bupivicaine, lidocaine, dexamethasone, a non-steroidal antiinflammatory agent, an antibiotic, an immunomodulator, a bone morphogenic protein, a cytokine, a growth factor, a vascular endothelial growth factor, and combinations of these.

Example 6

An exemplary device may be affixed in the joint implantation into a pre-drilled bone tunnel. In such an embodiment, the outer shell of the device includes a bone anchor design with axially aligned and concentrically spaced barbs.

Example 7

In some embodiments, a sustained release device for a joint is deployed in an ambulatory setting, such as an office-based ambulatory surgical suite. The specific point of insertion will be identified using orthogonal radiography or stereotactic CT scanning. An injector gun will be used to pre-drill and then insert the device into the bone tunnel.

Example 8

Figure 14:
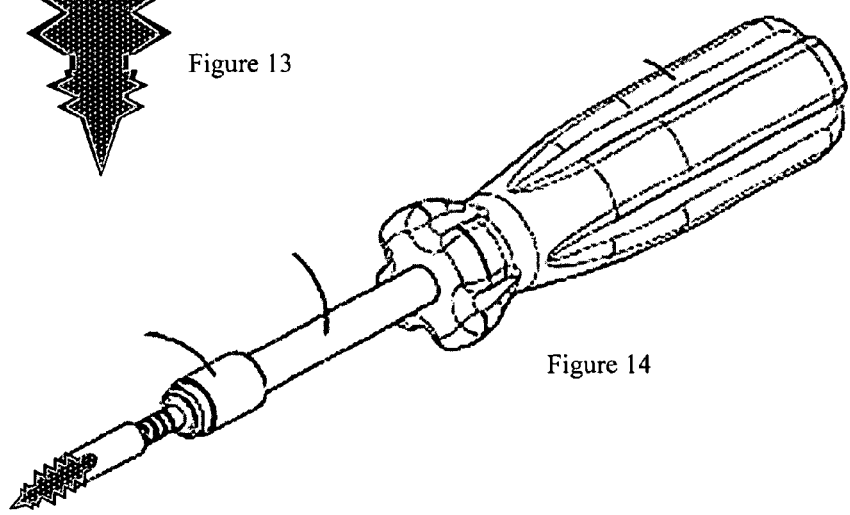
FIG. 14 depicts an exemplary insertion device for a drug delivery device.

In a typical procedure, the device may be inserted in a minor procedure or ambulatory surgical setting via a percutaneous delivery gun, using an insertion device (such as depicted in FIG. 14). The specific target attachment zone can be identified by palpation of anatomic landmarks and/or radiographically by orthogonal plain radiographs, computerized tomographic imaging, or three dimensional computerized tomographic imaging and localization, or by other localization techniques. Local anesthetic can be administered into the skin and subcutaneous tissues and into the synovium. A stab incision may be made in the skin. Blunt dissection may then be carried down through subcutaneous tissue. A cannulated trochar may then be used to penetrate the joint capsule. The trochar may be advanced to the target delivery site identified previously. The delivery gun or insertion device may be placed into the cannula of the trochar. A bone tunnel may be pre-drilled or the implant directly inserted into the bone of the attachment zone. If the device has outer threads, such as shown in FIG. 11, it may be seated by using those self tapping and self boring outer threads of the stage. The surgical wound may then be closed using conventional techniques.

Example 9

A drug insert may be replaced by a minor surgical procedure. Surgical access may be gained to the device—i.e., anesthesia, incision, dissection, and capsule penetration using a cannulated trocar. A drug insert retrieval device may be placed in the trocar and advanced to the device. The drug insert may be impaled or otherwise attached to the retrieval device, which may then be withdrawn to remove the drug insert. A replacement drug insert, mounted on a drug insert placement device (which may be the same as the drug insert retrieval device), may then be placed in the cannula and advanced to the attached drug delivery device.

Example 10

A drug insert can include a polymer solution/drug mixture having a polymer and a co-dissolved or suspended drug. This drug/polymer insert may be constructed by forming a polymer solution/drug mixture including a polymer-dissolved in an organic solvent and a co-dissolved or suspended drug and then removing the solvent from the polymer solution/drug mixture to form the solid polymer/drug matrix. The polymer can be any biocompatible polymer, such as poly(lactic acid) or a poly(lactic acid-co-glycolic acid) copolymer. The drug can be a therapeutic, prophylactic or diagnostic agent, such as a protein, nucleic acid or small organic molecule.

Example 11

A drug insert may include dexamethasone and polylactic glycolic acid.

Example 12

A drug insert may include gentamycin and polylactic glycolic acid.

EQUIVALENTS

Those skilled in the art will recognize, or be able to ascertain using no more than routine experimentation, many equivalents to the specific embodiments and practices described herein. Such equivalents are intended to be encompassed by the following claims.

We claim:
1. A method of intra-articular drug delivery, comprising:
identifying an attachment zone in a synovial joint, wherein the attachment zone comprises a non-articulating portion of bone and/or cartilage within the synovial joint; and
percutaneously affixing a drug release device in the attachment zone, the drug release device comprising a base affixable in the attachment zone, a sustained-release drug carrier, and a drug, the device positioned so that the device releases the drug into the synovial fluid of the synovial joint, and so that agitation of the synovial fluid facilitates elution of the drug from the drug release device.
2. The method of claim 1, further comprising removing the bone and/or cartilage in the attachment zone to create a void, and so inserting the drug release device into the void that at least one surface of the drug release device is in communication with the synovial fluid.
3. The method of claim 2, wherein the drug release device is so inserted that its surface in communication with the synovial fluid is about flush with surrounding bone and/or cartilage.
4. The method of claim 1, wherein the attachment zone comprises a band of bone and/or cartilage adjacent to an articulating surface within the synovial joint.
5. The method of claim 4, wherein the band extends from about 0.5 millimeters to about 1 centimeter away from the articulating surface.
6. The method of claim 4, further comprising removing the bone and/or cartilage in the attachment zone to create a void, and so inserting the drug release device into the void that at least one surface of the drug release device is in communication with the synovial fluid.
7. The method of claim 6, wherein the drug release device is so inserted that its surface in communication with the synovial fluid is about flush with surrounding bone and/or cartilage.
8. The method of claim 1, wherein the synovial joint is a hip joint, and the attachment zone comprises a non-articulating portion of bone and/or cartilage within the hip.
9. The method of claim 8, wherein the attachment zone comprises a band of bone and/or cartilage adjacent to at least one of a femoral head, and an acetabulum.
10. The method of claim 1, wherein the synovial joint is a knee joint, and the attachment zone comprises a non-articulating portion of bone and/or cartilage within the knee.
11. The method of claim 10, wherein the attachment zone comprises a band of bone and/or cartilage adjacent to at least one of a tibial plateau, a femoral condyle, a patellofemoral area, the medial rim of a femoral trochlea, the lateral rim of a femoral trochlea, and the periphery of an intercondylar notch.

12. The method of claim 1, wherein the synovial joint is a shoulder joint, and the attachment zone comprises a non-articulating portion of bone and/or cartilage within the shoulder.

13. The method of claim 12, wherein the attachment zone comprises a band of bone and/or cartilage adjacent to at least one of the anatomical neck of a humerus, a glenoid cavity, and a glenoid neck.

14. The method of claim 1, wherein the synovial joint is an arthroplastic joint comprising at least one prosthesis, and the attachment zone comprises a non-articulating portion of bone and/or cartilage within the joint.

15. The method of claim 14, wherein the attachment zone comprises a band of bone and/or cartilage adjacent to the at least one prosthesis.

16. The method of claim 1, wherein the drug release device is forcefully injected by gun.

17. The method of claim 1, wherein the drug release device comprises threads on its outer surface, and the drug release device is affixed by drilling a hole in the attachment zone and screwing the drug release device into the hole.

18. A method of intra-articular drug delivery, comprising:
identifying a para-articular attachment zone in a synovial joint, wherein the attachment zone comprises a non-articulating portion of bone and/or cartilage within the synovial joint;
creating a void in the para-articular attachment zone; and
percutaneously implanting in the void a drug-release means for sustainedly releasing a drug into the synovial fluid of the synovial joint.

* * * * *